United States Patent
Hess

(10) Patent No.: US 8,075,593 B2
(45) Date of Patent: Dec. 13, 2011

(54) INTERSPINOUS IMPLANTS AND METHODS FOR IMPLANTING SAME

(75) Inventor: Harold Hess, Overland Park, KS (US)

(73) Assignee: Spinal Simplicity LLC, Overland Park, KS (US)

(*) Notice: Subject to any disclaimer, the term of this patent is extended or adjusted under 35 U.S.C. 154(b) by 988 days.

(21) Appl. No.: 12/011,905

(22) Filed: Jan. 30, 2008

(65) Prior Publication Data

US 2009/0054988 A1    Feb. 26, 2009

Related U.S. Application Data

(60) Provisional application No. 61/007,916, filed on May 1, 2007, provisional application No. 60/959,799, filed on Jul. 16, 2007, provisional application No. 60/961,780, filed on Jul. 24, 2007, provisional application No. 61/000,831, filed on Oct. 29, 2007, provisional application No. 61/001,430, filed on Nov. 1, 2007.

(51) Int. Cl.
*A61B 17/70* (2006.01)

(52) U.S. Cl. .................. 606/248; 623/17.11; 623/17.16

(58) Field of Classification Search .......... 606/246–279, 606/63, 66, 68, 310, 323, 326, 327; 623/17.11–17.16; 411/24–25, 32, 340
See application file for complete search history.

(56) References Cited

U.S. PATENT DOCUMENTS

| | | | |
|---|---|---|---|
| 4,599,086 A | 7/1986 | Doty | |
| 4,721,103 A | 1/1988 | Freedland | |
| 4,998,936 A | 3/1991 | Mehdian et al. | |
| 5,514,180 A | 5/1996 | Heggeness et al. | |
| 5,645,599 A | 7/1997 | Samani | |
| 5,653,761 A | 8/1997 | Pisharodi | |
| 5,702,391 A * | 12/1997 | Lin | 623/17.11 |
| 5,800,547 A * | 9/1998 | Schafer et al. | 623/17.16 |
| 5,836,948 A | 11/1998 | Zucherman et al. | |
| 5,849,004 A * | 12/1998 | Bramlet | 606/232 |
| 5,860,977 A | 1/1999 | Zucherman et al. | |
| 5,876,404 A | 3/1999 | Zucherman et al. | |

(Continued)

FOREIGN PATENT DOCUMENTS

WO    WO-2008/088613 A2    7/2008

(Continued)

OTHER PUBLICATIONS

Medtronic: CD Horizon SPIRE (Trademark), Stabilization System, Information Brochure, James Robinson, MD, 2006.

(Continued)

*Primary Examiner* — Eduardo C Robert
*Assistant Examiner* — Michelle C. Eckman
(74) *Attorney, Agent, or Firm* — Scott D. Wofsy; George N. Chaclas; Edwards Wildman Palmer LLP

(57) ABSTRACT

A spinal implant for treating lumbar spinal stenosis or as an adjunct to spinal fusion. The implant includes a body portion having an interior cavity. A plurality of locking wings are adapted and configured to move between a stowed position retracted within the interior cavity of the body portion and a deployed position extended from the interior cavity of the body portion. In the deployed position, the wings fix the implant in a selected interspinous space. A cable and wheel arrangement moves the plurality of locking wings from the stowed position to the deployed position and a ratchet/pawl assembly prevents backward movement of the wings.

11 Claims, 27 Drawing Sheets

U.S. PATENT DOCUMENTS

| | | |
|---|---|---|
| 5,876,457 A | 3/1999 | Picha et al. |
| 5,904,686 A | 5/1999 | Zucherman et al. |
| 5,968,098 A | 10/1999 | Winslow |
| 6,017,342 A | 1/2000 | Rinner |
| 6,045,552 A | 4/2000 | Zucherman et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,090,112 A | 7/2000 | Zucherman et al. |
| 6,093,207 A | 7/2000 | Pisharodi |
| 6,149,652 A | 11/2000 | Zucherman et al. |
| 6,152,926 A | 11/2000 | Zucherman et al. |
| 6,156,038 A | 12/2000 | Zucherman et al. |
| 6,174,334 B1 | 1/2001 | Suddaby |
| 6,183,471 B1 | 2/2001 | Zucherman et al. |
| 6,190,387 B1 | 2/2001 | Zucherman et al. |
| 6,235,030 B1 | 5/2001 | Zucherman et al. |
| 6,238,397 B1 | 5/2001 | Zucherman et al. |
| 6,245,108 B1 | 6/2001 | Biscup |
| 6,264,677 B1 | 7/2001 | Simon et al. |
| 6,280,444 B1 | 8/2001 | Zucherman et al. |
| 6,332,882 B1 | 12/2001 | Zucherman et al. |
| 6,332,883 B1 | 12/2001 | Zucherman et al. |
| 6,379,355 B1 | 4/2002 | Zucherman et al. |
| 6,402,750 B1 | 6/2002 | Atkinson et al. |
| 6,419,676 B1 | 7/2002 | Zucherman et al. |
| 6,419,677 B2 | 7/2002 | Zucherman et al. |
| 6,451,019 B1 | 9/2002 | Zucherman et al. |
| 6,451,020 B1 | 9/2002 | Zucherman et al. |
| 6,478,796 B2 | 11/2002 | Zucherman et al. |
| 6,500,178 B2 | 12/2002 | Zucherman et al. |
| 6,514,256 B2 | 2/2003 | Zucherman et al. |
| 6,610,092 B2 | 8/2003 | Ralph et al. |
| 6,626,944 B1 | 9/2003 | Taylor |
| 6,652,527 B2 | 11/2003 | Zucherman et al. |
| 6,652,534 B2 | 11/2003 | Zucherman et al. |
| 6,682,564 B1 | 1/2004 | Duarte |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,709,435 B2 | 3/2004 | Lin |
| 6,712,819 B2 | 3/2004 | Zucherman et al. |
| 6,733,534 B2 | 5/2004 | Sherman |
| 6,743,256 B2 | 6/2004 | Mason |
| 6,746,485 B1 | 6/2004 | Zucherman et al. |
| 6,761,720 B1 | 7/2004 | Senegas |
| 6,770,096 B2 | 8/2004 | Bolger et al. |
| 6,783,546 B2 | 8/2004 | Zucherman et al. |
| 6,796,983 B1 | 9/2004 | Zucherman et al. |
| 6,849,093 B2 | 2/2005 | Michelson |
| 6,860,977 B2 | 3/2005 | Heinz et al. |
| 6,902,566 B2 | 6/2005 | Zucherman et al. |
| 6,926,728 B2 | 8/2005 | Zucherman et al. |
| 6,946,000 B2 | 9/2005 | Senegas et al. |
| 6,949,123 B2 | 9/2005 | Reiley |
| 7,029,473 B2 | 4/2006 | Zucherman et al. |
| 7,041,135 B2 | 5/2006 | Michelson |
| 7,083,649 B2 | 8/2006 | Zucherman et al. |
| 7,101,375 B2 | 9/2006 | Zucherman et al. |
| 7,125,425 B2 | 10/2006 | Foley et al. |
| 7,189,234 B2 | 3/2007 | Zucherman et al. |
| 7,192,446 B2 | 3/2007 | Shapiro et al. |
| 7,201,751 B2 | 4/2007 | Zucherman et al. |
| 7,217,291 B2 | 5/2007 | Zucherman et al. |
| 7,232,464 B2 | 6/2007 | Mathieu et al. |
| 7,238,186 B2 | 7/2007 | Zdeblick et al. |
| 7,238,204 B2 | 7/2007 | Le Couedic et al. |
| 7,306,628 B2 | 12/2007 | Zucherman et al. |
| 7,320,707 B2 | 1/2008 | Zucherman et al. |
| 7,326,248 B2 | 2/2008 | Michelson |
| 7,410,501 B2 | 8/2008 | Michelson |
| 7,423,268 B2 | 9/2008 | Ren |
| 7,445,636 B2 | 11/2008 | Michelson |
| 7,445,637 B2 | 11/2008 | Taylor |
| 7,465,317 B2 | 12/2008 | Malberg et al. |
| 7,465,318 B2 | 12/2008 | Sennett et al. |
| 7,476,251 B2 | 1/2009 | Zucherman et al. |
| 7,481,839 B2 | 1/2009 | Zucherman et al. |
| 7,481,840 B2 | 1/2009 | Zucherman et al. |
| 7,497,859 B2 | 3/2009 | Zucherman et al. |
| 7,503,935 B2 | 3/2009 | Zucherman et al. |
| 7,510,567 B2 | 3/2009 | Zucherman et al. |
| 7,520,899 B2 | 4/2009 | Zucherman et al. |
| 7,662,187 B2 | 2/2010 | Zucherman et al. |
| 2004/0024463 A1 | 2/2004 | Thomas et al. |
| 2004/0193158 A1 | 9/2004 | Lim et al. |
| 2005/0049590 A1* | 3/2005 | Alleyne et al. ............... 606/61 |
| 2005/0080425 A1 | 4/2005 | Bhatnagar et al. |
| 2005/0196420 A1 | 9/2005 | Zucherman et al. |
| 2005/0245929 A1 | 11/2005 | Winslow et al. |
| 2006/0036258 A1 | 2/2006 | Zucherman et al. |
| 2006/0064165 A1 | 3/2006 | Zucherman et al. |
| 2006/0064166 A1 | 3/2006 | Zucherman et al. |
| 2006/0084985 A1 | 4/2006 | Kim |
| 2006/0089718 A1 | 4/2006 | Zucherman et al. |
| 2006/0095136 A1* | 5/2006 | McLuen ................ 623/23.47 |
| 2006/0195102 A1 | 8/2006 | Malandain |
| 2006/0247634 A1 | 11/2006 | Warner et al. |
| 2006/0264938 A1* | 11/2006 | Zucherman et al. ........... 606/61 |
| 2006/0264939 A1 | 11/2006 | Zucherman et al. |
| 2006/0265067 A1 | 11/2006 | Zucherman et al. |
| 2006/0271049 A1* | 11/2006 | Zucherman et al. ........... 606/61 |
| 2006/0271194 A1 | 11/2006 | Zucherman et al. |
| 2007/0010813 A1* | 1/2007 | Zucherman et al. ........... 606/61 |
| 2007/0032790 A1* | 2/2007 | Aschmann et al. ............ 606/61 |
| 2007/0055291 A1 | 3/2007 | Birkmeyer et al. |
| 2007/0093830 A1 | 4/2007 | Zucherman et al. |
| 2007/0185490 A1 | 8/2007 | Implicito |
| 2007/0225706 A1* | 9/2007 | Clark et al. ................. 606/61 |
| 2008/0027148 A1* | 1/2008 | Abdou ....................... 606/61 |
| 2008/0108990 A1* | 5/2008 | Mitchell et al. ............... 606/61 |
| 2008/0132949 A1* | 6/2008 | Aferzon et al. ............. 606/246 |
| 2008/0177306 A1* | 7/2008 | Lamborne et al. .......... 606/246 |
| 2008/0243250 A1 | 10/2008 | Seifert et al. |
| 2008/0281359 A1 | 11/2008 | Abdou |
| 2008/0312741 A1* | 12/2008 | Lee et al. .................. 623/17.11 |
| 2009/0234389 A1* | 9/2009 | Chuang et al. .............. 606/249 |
| 2009/0281626 A1 | 11/2009 | Farr |
| 2010/0057130 A1* | 3/2010 | Yue .............................. 606/249 |
| 2010/0114166 A1* | 5/2010 | Kohm et al. ................. 606/247 |
| 2011/0160773 A1* | 6/2011 | Aschmann et al. .......... 606/249 |
| 2011/0190817 A1* | 8/2011 | Thommen et al. ........... 606/249 |

FOREIGN PATENT DOCUMENTS

WO    WO-2009/132059 A1    10/2009

OTHER PUBLICATIONS

St. Francis Medical Technologies, Inc., "A Patient's Guide to Lumbar Spinal Stenosis," & "X STOP (Trademark)—Interspinous Process Decompression," Information Guide, Sep. 16, 2005.

International Search Report in PCT/US09/006742 dated Apr. 16, 2010.

Written Opinion in PCT/US09/006742 dated Apr. 16, 2010.

International Search Report in PCT/US08/01231 dated Aug. 29, 2008.

Written Opinion in PCT/US08/01231 dated Aug. 29, 2008.

European Search Report (EP No. 08724975.1) mailed on Oct. 29, 2010 which corresponds to PCT/US2008/01231 (7 pages).

US 7,520,878, 04/2009, Michelson (withdrawn)

\* cited by examiner

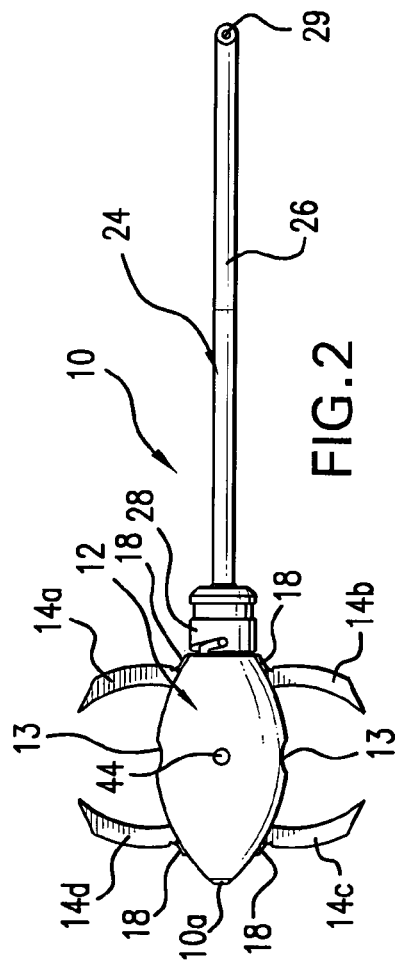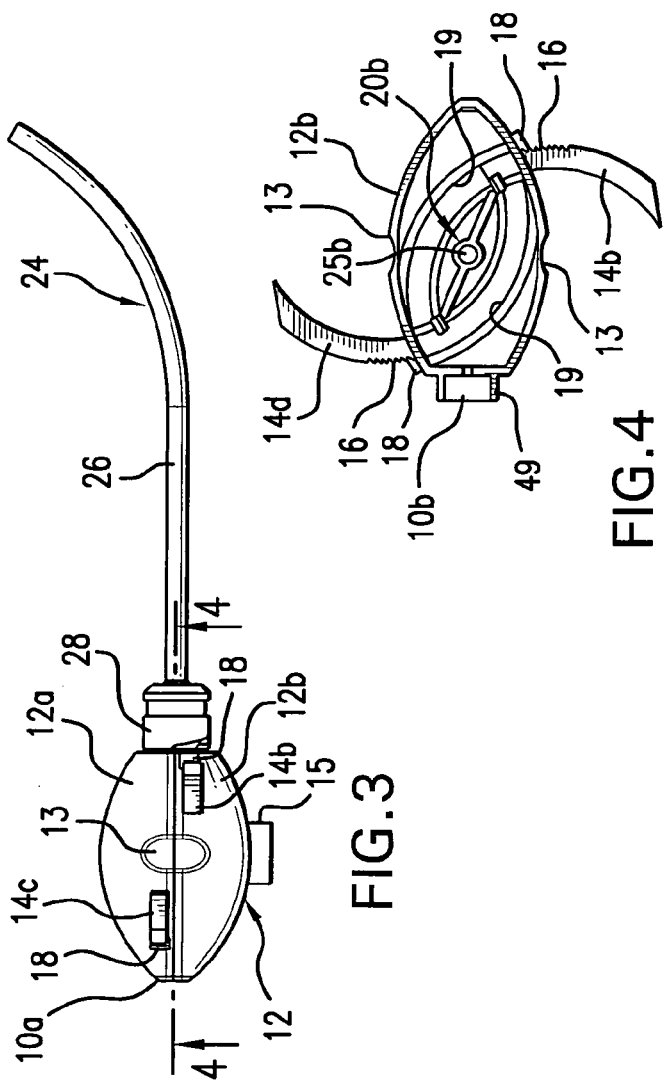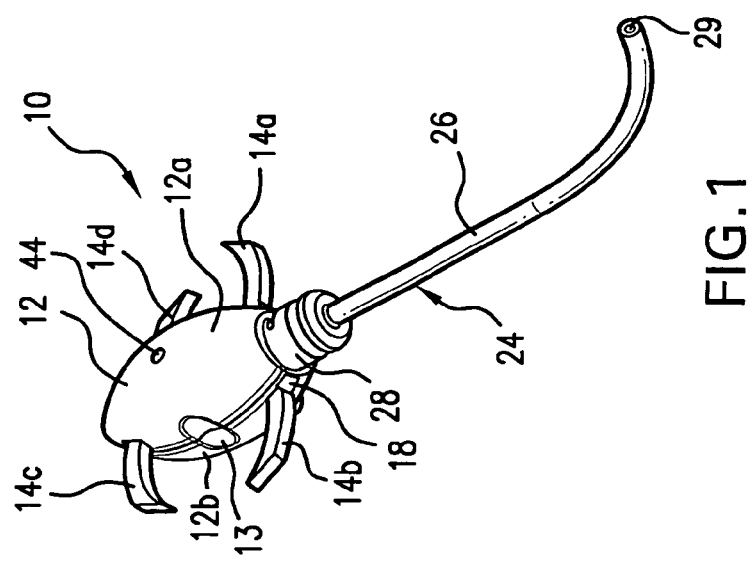

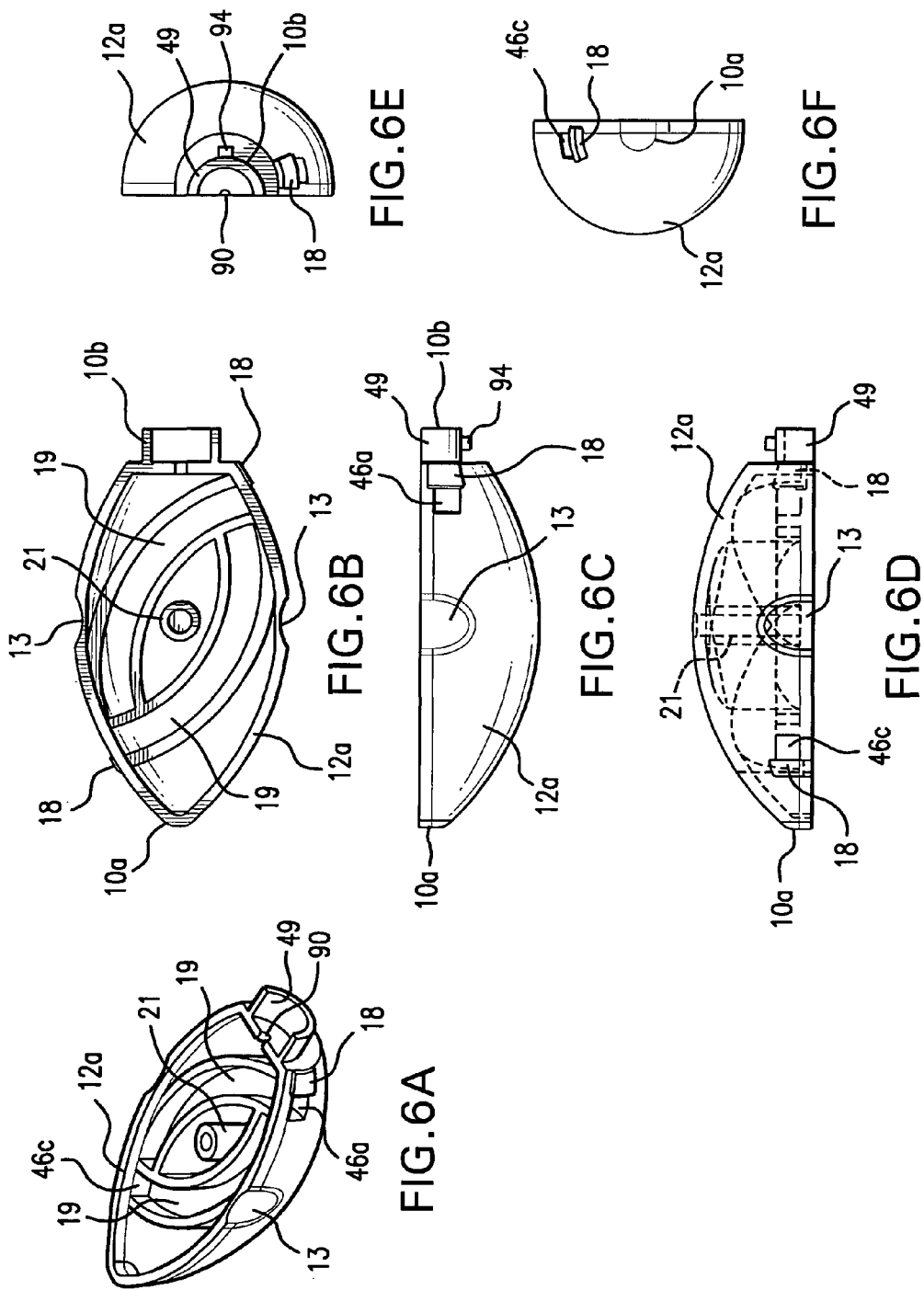

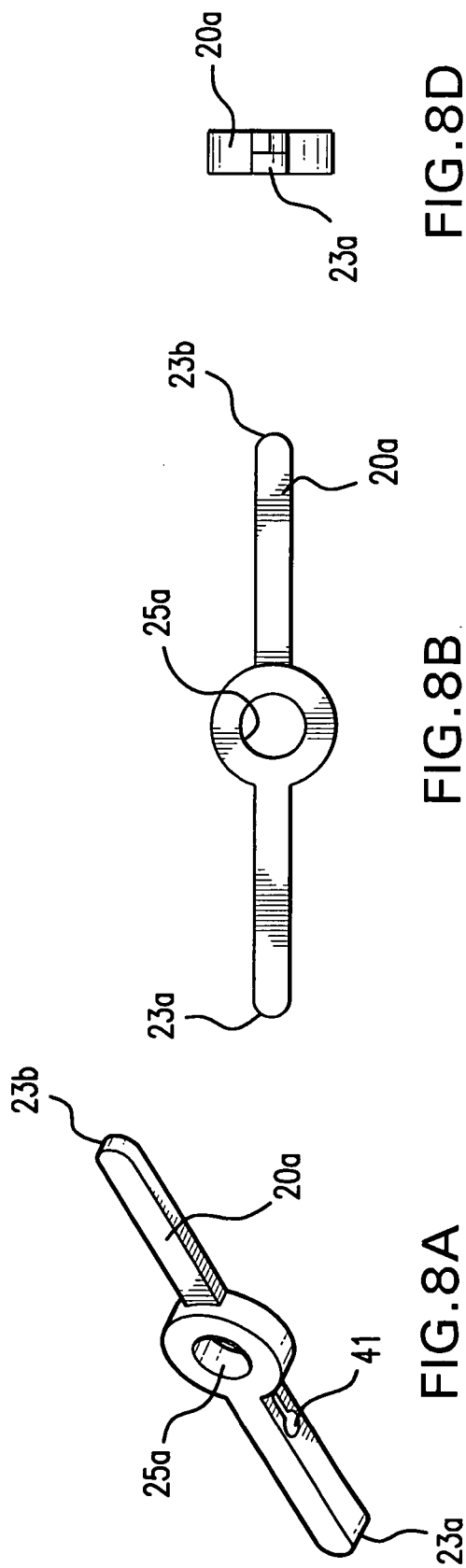

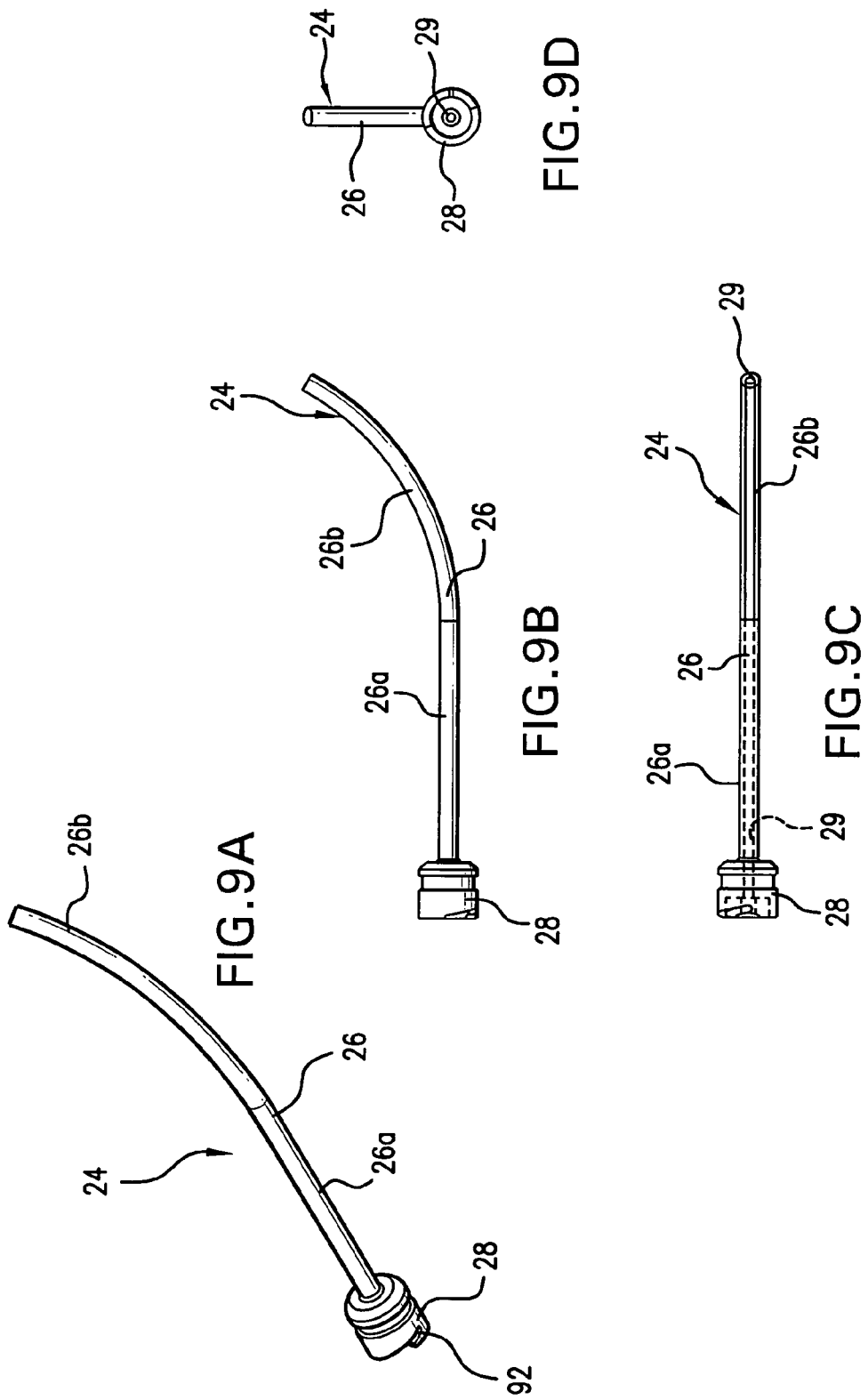

INTERSPINOUS IMPLANTS AND METHODS FOR IMPLANTING SAME

CROSS-REFERENCE TO RELATED APPLICATION

This application claims priority to the following applications: U.S. patent application Ser. No. 11/743,086, filed May 1, 2007; U.S. Provisional Patent Application No. 60/959,799, filed Jul. 16, 2007; U.S. Provisional Patent Application No. 60/961,780, filed Jul. 24, 2007; U.S. Provisional Patent Application No. 61/000,831, filed Oct. 29, 2007; and U.S. Provisional Patent Application No. 61/001,430, filed Nov. 1, 2007, each of which is incorporated herein by reference.

BACKGROUND OF THE INVENTION

1. Field of the Invention

The subject invention is directed to spinal implants, and more particularly, to an interspinous implant with deployable wings for treating lumbar spinal stenosis, methods for the percutaneous implantation of the interspinous implant, and techniques for determining an appropriate size of the interspinous implant.

2. Description of Related Art

The spine consists of a column of twenty-four vertebrae that extend from the skull to the hips. Discs of soft tissue are disposed between adjacent vertebrae. The vertebrae provide support for the head and body, while the discs act as cushions. In addition, the spine encloses and protects the spinal cord, which is surrounded by a bony channel called the spinal canal. There is normally a space between the spinal cord and the borders of the spinal canal so that the spinal cord and the nerves associated therewith are not pinched.

Over time, the ligaments and bone that surround the spinal canal can thicken and harden, resulting in a narrowing of the spinal canal and compression of the spinal cord. This condition is called spinal stenosis, which results in pain and numbness in the back and legs, weakness and/or a loss of balance. These symptoms often increase after walking or standing for a period of time.

There are number of non-surgical treatments of stenosis. These include non-steroidal anti-inflammatory drugs to reduce the swelling and pain, and corticosteroid injections to reduce swelling and treat acute pain. While some patients may experience relief from symptoms of spinal stenosis with such treatments, many do not, and thus turn to surgical treatment. The most common surgical procedure for treating spinal stenosis is decompressive laminectomy, which involves removal of parts of the vertebrae. The goal of the procedure is to relieve pressure on the spinal cord and nerves by increasing the area of the spinal canal.

Interspinous process decompression (IPD) is a less invasive surgical procedure for treating spinal stenosis. With IPD surgery, there is no removal of bone or soft tissue. Instead, an implant or spacer device is positioned behind the spinal cord between the spinous process that protrudes from the vertebrae in the lower back. A well-known implant used for performing IPD surgery is the X-STOP® device, which was first introduced by St. Francis Medical Technologies, Inc. of Alameda Calif. However, implantation of the X-STOP® device still requires an incision to access the spinal column to deploy the X-STOP® device.

It would be advantageous to provide an implant for performing IPD procedures that could be percutanously inserted into the interspinous space and effectively treat lumbar spinal stenosis.

SUMMARY OF THE INVENTION

The subject invention is directed to a spinal implant used primarily for interspinous process decompression procedures that can be percutaneously introduced into the interspinous space. In its most basic configuration, the device includes a body portion having an interior cavity, a plurality of locking wings adapted and configured to move between a stowed position retracted within the interior cavity of the body portion and a deployed position extended from the interior cavity of the body portion, and means for moving the plurality of locking wings from the stowed position to the deployed position.

The subject invention is also directed to a method of percutaneously placing a spinal implant during an interspinous process decompression procedure, which includes, among others, the steps of providing a spinal implant having a body portion containing a plurality of deployable locking wings that are dimensioned and configured to engage the spinous processes of adjacent vertebrae at symptomatic disc levels, advancing a curved stylet through the skin from one side of the spine down into the spinous processes between the symptomatic disc levels, guiding the spinal implant along the path defined by the curved stylet into the spinous processes from a unilateral approach, and subsequently deploying the locking wings to engage the spinous processes of adjacent vertebrae.

The subject invention is further directed to a method of percutaneously placing a spinal implant that includes the steps of providing a spinal implant having a body portion containing a plurality of deployable locking wings dimensioned and configured to engage the spinous processes of adjacent vertebrae at symptomatic disc levels, advancing a curved stylet through the skin from one side of the spine, down into the spinous process between the symptomatic disc levels and out through the skin on the opposite side of the spine, so as to enable a bilateral approach to the spinous process. The method further includes the steps of guiding the spinal implant along the path defined by the curved stylet into the spinous processes from either side of the spine and subsequently deploying the locking wings to engage the spinous processes of adjacent vertebrae.

The implant may be advantageously used for various treatments including as an adjunct to a fusion, for treatment of back pain and as a treatment to alleviate symptoms of a protruding lumbar disc.

The subject invention is further directed to a tool kit for facilitating the percutaneous implantation of the device. The kit includes one or more of the following components: a stylet assembly having a graduated positioning stylet, a curved stylet and an adjustable bridging portion with curved guide sleeve for the curved stylet. The kit may further include a set of curved tubular dilators of varying diameter and a plurality of implants of varying size.

The subject invention is also directed to an apparatus for measuring the optimum size of an interspinous implant for treating lumbar spinal stenosis. The apparatus includes distracting means dimensioned and configured for percutaneous insertion into the interspinous space between adjacent spinous processes, wherein the distracting means is movable between a closed insertion position and an open distracting position. The apparatus further includes deployment means for moving the distracting means between the closed insertion position and the open detracting position, wherein an amount of movement of the deployment means corresponds to an optimum size of interspinous implant for placement in the interspinous space between the adjacent spinous processes.

The subject invention is also directed to a method for measuring the optimum size of an interspinous implant for treating lumbar spinal stenosis. The method includes the step of percutaneously inserting distracting means into the interspinous space between adjacent spinous processes, wherein the distracting means is movable between a closed insertion position and an open distracting position. The method further includes the step of moving the distracting means between the closed insertion position and the open detracting position, and then correlating movement of the distracting means to an optimum size of interspinous implant for placement in the interspinous space between adjacent spinous processes.

In one embodiment, the subject technology is directed to an interspinous implant for placement between spinous processes of symptomatic disc levels including a shell having upper and lower shell portions defining four interior grooves that terminate in openings in the shell, the shell having a pawl adjacent each opening. Four deployable ratcheting locking wings slidably couple in a respective groove between: i) a stowed position in which the wings are within the grooves; and ii) a deployed position in which the wings extend outward from the shell. Each wing has a set of ratchet teeth for engaging and locking the respective pawl in the deployed position. A pair of coaxial locking wheels rotatably mount in the shell to selectively exert a force against each locking wing to move the locking wings from the stowed to the deployed position and a deployment cable couples to the wheels to actuate rotation of the wheels.

The implant may further have a guide on the shell for accommodating a stylet during a percutaneous placement procedure. Additionally, two wings may be located on first parallel, spaced apart geometric planes that extend on a first side of a centerline of the shell, with the other two wings are located on second parallel, spaced apart geometric planes that extend on a second side of the centerline of the shell. The interspinous implant may also include a placement tool for introducing the shell into the spinous process. The placement tool may include an elongated tubular stem having a straightened distal portion and a curved proximal portion that form a central lumen for accommodating the deployment cable and a coupling sleeve on the straightened distal portion for selectively engaging the shell. In another embodiment, the placement tool may be an elongated tubular stem that is curved.

The interspinous implant may also include a stylet assembly for percutaneous insertion of the interspinous implant. The stylet assembly includes an elongated graduated positioning stylet for setting a position of the stylet assembly over a central axis of a spine, a curved stylet for gaining lateral access to an interspinous space and an adjustable guide bridge having a central portion extending between the positioning stylet and the curved stylet for guiding the positioning stylet, the bridge also having a curved guide sleeve for guiding the curved stylet. The curved stylet may be sized and configured for a unilateral or bilateral insertion.

The interspinous implant may also include an actuating mechanism including an elongated, arcuate, hollow cable attachment device having a tapered distal end with radially inwardly extending flexible prongs that form a distal opening, a deployment cable having a distal end attached to the interspinous implant and a proximal end having a ball captured by the flexible prongs and a second tube for insertion into the cable attachment device to deflect the flexible prongs and, in turn, release the ball therefrom after deployment of the interspinous implant.

In another embodiment, the subject technology is directed to a method of placing a spinal implant comprising the steps of: providing a spinal implant having a body portion containing a plurality of deployable locking wings dimensioned and configured to engage the spinous processes of adjacent vertebrae at symptomatic disc levels; advancing a curved stylet through the skin from one side of the spine down into the spinous processes between the symptomatic disc levels; guiding the spinal implant along a path defined by the curved stylet into the spinous processes from a unilateral approach; and deploying the locking wings to engage the spinous processes of adjacent vertebrae.

In still one more embodiment, the subject technology is directed to a device for measuring percutaneously an optimum size of an interspinous implant. The measuring device includes a proximal deployment portion including a plunger tube carrying a rod, a distal measuring assembly including four connected arms pivotally connected at four coupling joints, a central shaft connected to the rod of the plunger tube a proximal end and connected to the coupling joint on a distal end and two opposed concave cradles adjacent opposed coupling joints adapted to engage a spine when the rod and, in turn, the central shaft is pulled in a proximal direction while the plunger tube remains stationary, so that the connected arms expand from a closed to a measuring position. The measuring device may also include a strain gauge operatively associated with the plunger tube and rod for determining a force to be applied by an interspinous implant.

In another embodiment, the measuring device includes an elongated body portion having a pair of jaw members at a distal end thereof for positioning in the interspinous space, a cradle on each jaw member, the cradles being adapted and configured to cup an adjacent spinous process, a plunger tube and a rod partially housed within the plunger tube and attached to the jaw members for selectively moving the jaw members from a closed position to an open position in which the cradles engage the spinous process, wherein a travel distance of the rod within the plunger tube correlates to a length to which an interspinous space was distracted.

The subject technology also includes a method for measuring the optimum size of an interspinous implant for treating lumbar spinal stenosis including the steps of percutaneously inserting distracting means into the interspinous space between adjacent spinous processes, wherein the distracting means is movable between a closed insertion position and an open distracting position, moving the distracting means between the closed insertion position and the open detracting position and correlating movement of the distracting means to an optimum size of interspinous implant for placement in the interspinous space between adjacent spinous processes.

It is to be understood that each feature of the disclosed implants and methods may be interchanged and coupled freely with the various other features to utilize any combination thereof. These and other features of the interspinous implant and percutaneous placement method of the subject invention will become more readily apparent to those skilled in the art from the following detailed description of the preferred embodiment taken in conjunction with the drawings.

BRIEF DESCRIPTION OF THE DRAWINGS

So that those skilled in the art to which the subject invention appertains will readily understand how to make and use the interspinous implant of the subject invention without undue experimentation, preferred embodiments thereof will be described in detail hereinbelow with reference to certain figures, wherein:

FIG. 1 is a perspective view of an interspinous implant in accordance with the subject invention, which includes a main shell portion having a plurality of locking wings and an insertion tool to facilitate percutaneous introduction of the implant into the spine;

FIG. 2 is a top plan view of the interspinous implant of FIG. 1, illustrating the locking wings in a deployed position;

FIG. 3 is a side elevational view of the interspinous implant of FIG. 1;

FIG. 4 is a cross-sectional view taken along line 4-4 of FIG. 3 illustrating a locking wheel disposed within the main shell of the interspinous implant for deploying a pair of opposed lock wings;

FIG. 6A is a detailed perspective view of the upper portion of the main shell of the interspinous implant of FIG. 1;

FIG. 6B is a plan view of the inside of the upper portion of the main shell of FIG. 6A;

FIG. 6C is a side view of the inside of the upper portion of the main shell of FIG. 6A;

FIG. 6D is another side view of the inside of the upper portion of the main shell of FIG. 6A with the inside shown in phantom lines;

FIG. 6E is a proximal end view of the upper portion of the main shell of FIG. 6A;

FIG. 6F is a distal end view of the upper portion of the main shell of FIG. 6A;

FIG. 8A is a detailed perspective view of a locking wheel of the interspinous implant of FIG. 1;

FIG. 8B is a top view of the locking wheel of FIG. 8A;
FIG. 8C is a side view of the locking wheel of FIG. 8A;
FIG. 8D is an end view of the locking wheel of FIG. 8A.

FIG. 9A is a detailed perspective view of a placement tool for use with the interspinous implant of FIG. 1;

FIG. 9B is a side view of the placement tool of FIG. 9A;
FIG. 9C is a top view of the placement tool of FIG. 9A;
FIG. 9D is a distal end view of the placement tool of FIG. 9A;

DETAILED DESCRIPTION OF PREFERRED EMBODIMENTS

Figure 5A:
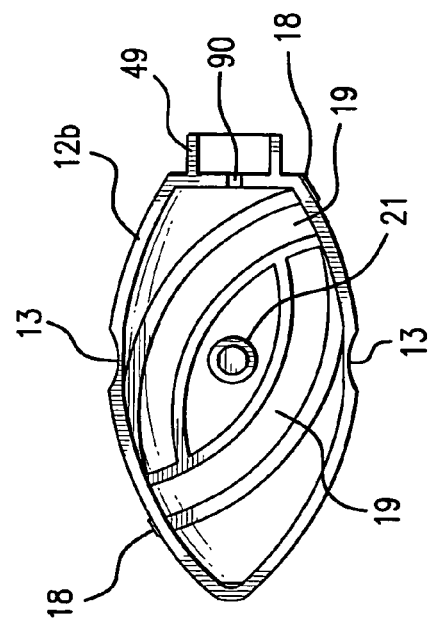
FIG. 5A is a detailed perspective view of the lower portion of the main shell of the interspinous implant of FIG. 1.

The present invention overcomes many of the prior art problems associated with implants to relieve spinal stenosis. The advantages, and other features of the system disclosed herein, will become more readily apparent to those having ordinary skill in the art from the following detailed description of certain preferred embodiments taken in conjunction with the drawings which set forth representative embodiments of the present invention and wherein like reference numerals identify similar structural elements. All relative descriptions herein such as horizontal, vertical, left, right, upper, and lower are with reference to the Figures, and not meant in a limiting sense. For reference, proximal is generally the area or portion adjacent or near the surgeon whereas distal refers to the portion remote or away from the surgeon.

Spinal Implant

Referring now FIG. 1, there is illustrated an interspinous implant constructed in accordance with a preferred embodiment of the subject invention and designated generally by reference numeral 10. Implant 10 is particularly well adapted for use in performing minimally invasive surgical procedures for treating spinal stenosis, including, for example, interspinous process decompression (IPD).

It is envisioned however, that the implant 10 of the subject invention can be used in other spinal procedures as well, including, but not limited to as an adjunct to spinal fusion procedures. Those skilled in the art will readily appreciate from the following description that the interspinous implant of the subject invention is well adapted for percutaneous insertion, and thus overcomes many of the deficiencies of prior art devices presently used in IPD procedures. That is, the implant 10 is dimensioned and configured for introduction and placement through a small stab skin incision.

Figure 5B:
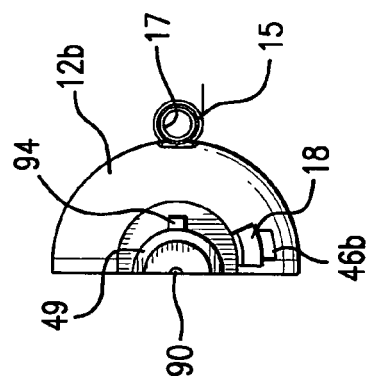
FIG. 5B is a plan view of the inside of the lower portion of the main shell of FIG. 5A.
Figure 5C:
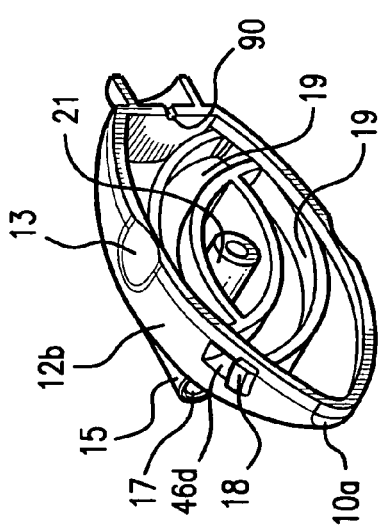
FIG. 5C is a side view of the inside of the lower portion of the main shell of FIG. 5A.
Figure 5D:
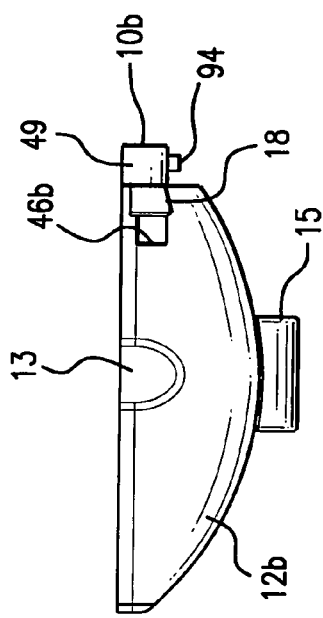
FIG. 5D is a proximal end view of the lower portion of the main shell of FIG. 5A.

Referring to FIGS. 1 through 4, the interspinous implant 10 of the subject invention includes a main shell or body portion 12 having upper and lower shell portions 12a, 12b. The shell portions 12a, 12b may have an interference fit or be held together by a fastener (not shown) inserted in a threaded hole 44. The shell portions 12a, 12b are preferably formed from a biocompatible polymeric material that has a modulus of elasticity that is substantially similar to that of bone, for example, polyetheretherketon thermoplastic (PEEK) or a similar material. The main shell 12 may also be made of a biocompatible metal such as a titanium alloy or like material. The main shell 12 is dimensioned and configured for placement between the spinous processes of symptomatic disc levels. (See also FIGS. 5A and 5B). Placement of the implant in this manner limits extension at the symptomatic levels, while preserving mobility and alignment. While the shell 12 has a generally bullet or frusto-conical shape, it is envisioned that the curved end section could be truncated or presented in a flattened orientation, whereby the shell would assume a barrel-shaped configuration among many other variations. The shell 12 has opposing depressions 13 that serve to match the profile of the adjacent bone when deployed.

The lower shell portion 12b includes an optional guide 15 for accommodating a stylet during a percutaneous placement procedure, as best seen in FIGS. 5A-5D and described in further detail below. The guide 15 has a bore 17 that can slide over a stylet. The main shell 12 houses four deployable ratcheting locking wings 14a-14d adapted and configured to engage adjacent vertebral portions of the spinous process. The shell 12 has four openings 46a-46d that allow the locking wings 14a-14d to extend outward from the shell 12. The locking wings 14a-14d are preferably formed from a light-weight, high-strength biocompatible material, such as, for example, titanium or a similar material.

Figure 10A:
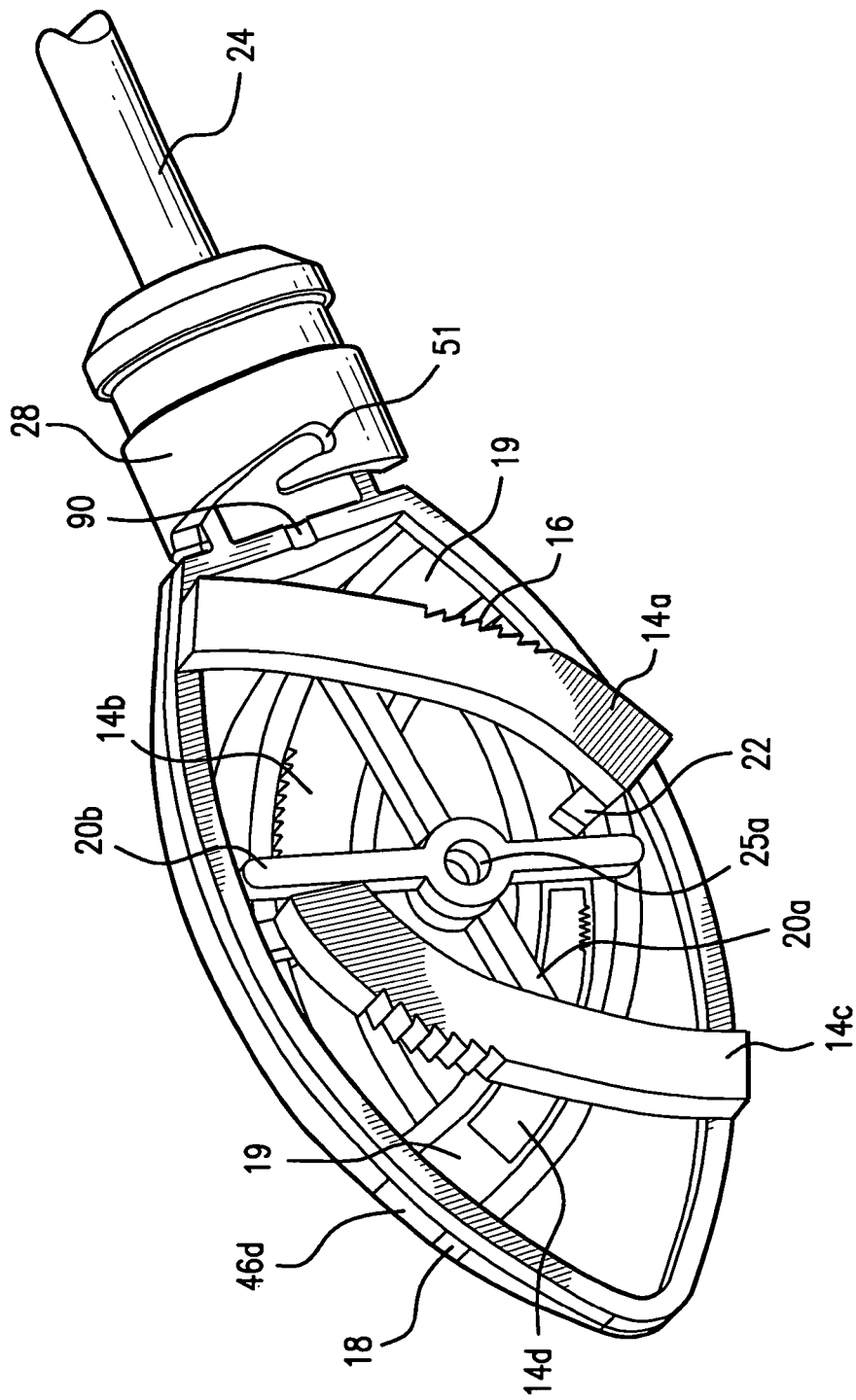
FIG. 10A is a perspective view of the interspinous implant of the subject invention, in cross-section to illustrate the four locking wings and two locking wheels in a stowed position.
Figure 10B:
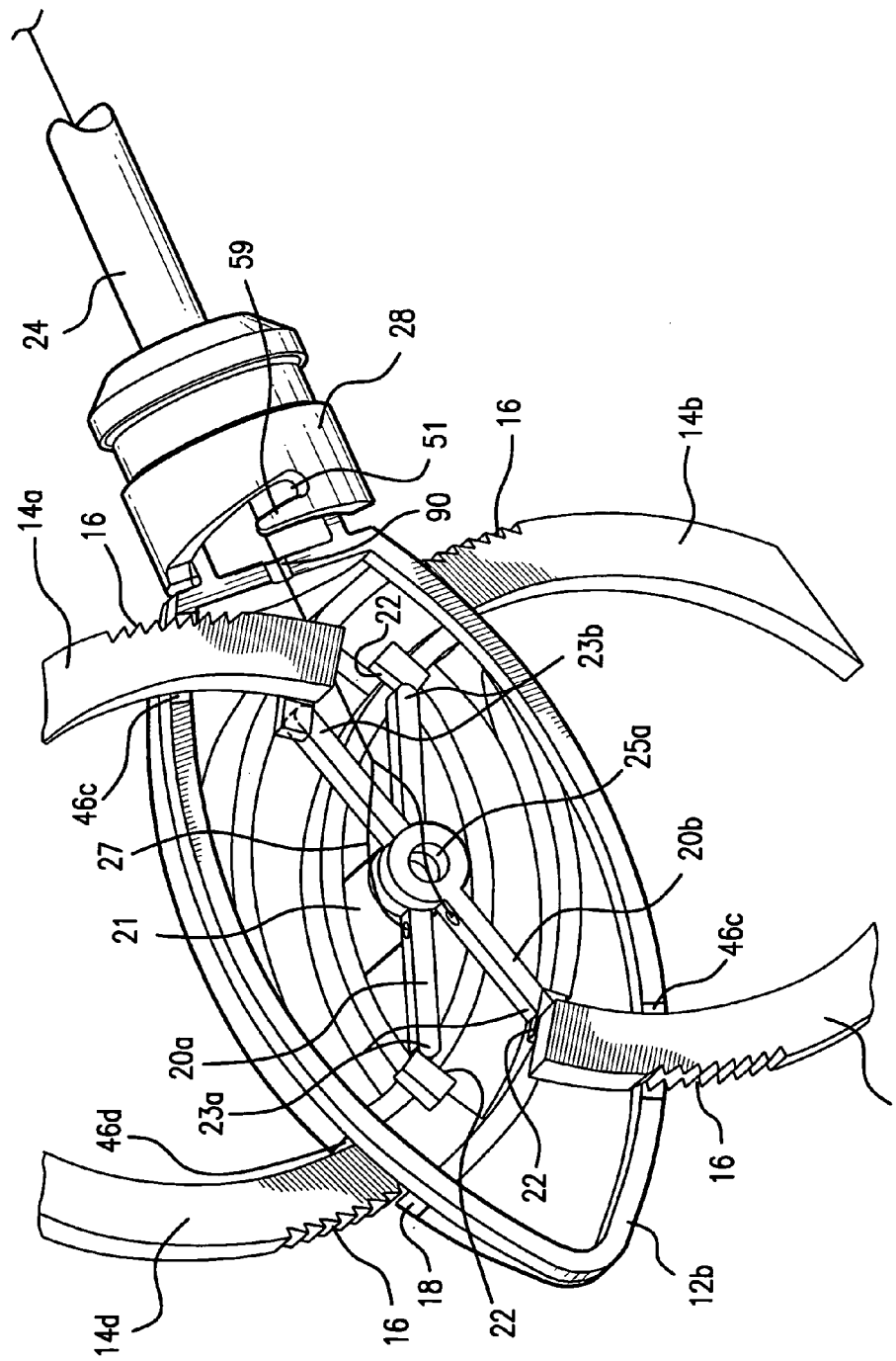
FIG. 10B is a perspective view of the interspinous implant of the subject invention, in cross-section to illustrate the four locking wings and two locking wheels in a deployed position.
Figure 11:
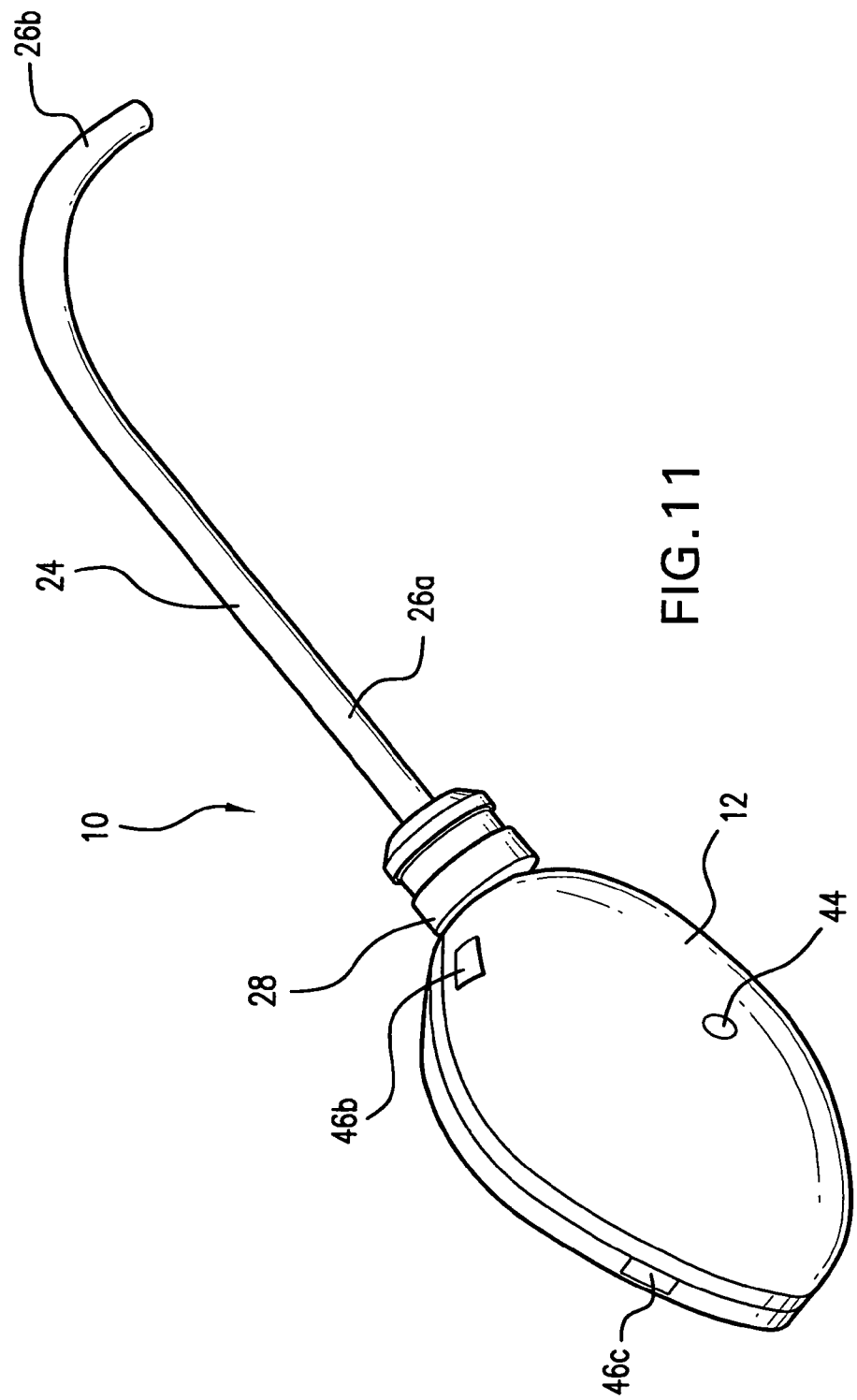
FIG. 11 is a perspective view of the interspinous implant of the subject invention, with the four locking wings fully retracted and stowed within the shell of the device.

During deployment of the implant 10, the locking wings 14a-14d are stowed within the shell 12 of the implant 10, as best seen in FIGS. 10A and 11, forming a streamlined structure. As best seen in FIGS. 4, 5A, 5B, 6A, 6B, 10A and 10B, two curved guide tracks 19 formed within the shell portions 12a, 12b accommodate the wings 14a-14d in the stowed position.

Figure 7E:
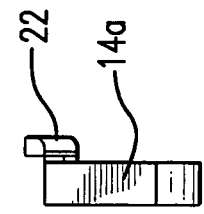
FIG. 7E is an end view of the locking wing of FIG. 7A.
Figure 7B:
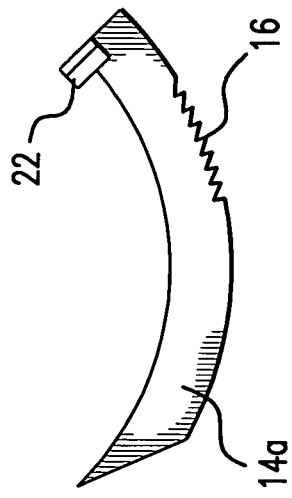
FIG. 7B is a side view of the locking wing of FIG. 7A.
Figure 7C:
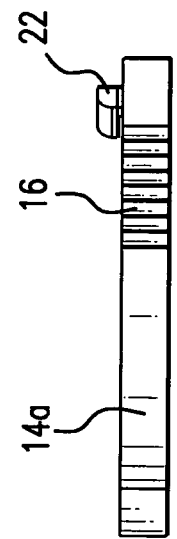
FIG. 7C is a top view of the locking wing of FIG. 7A.
Figure 7D:
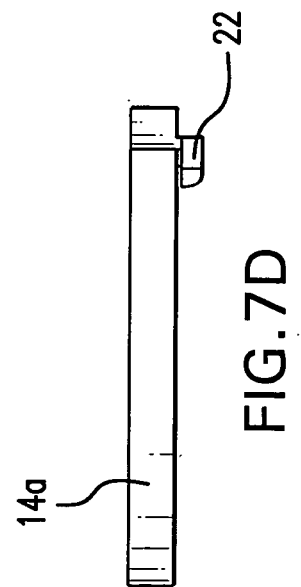
FIG. 7D is a bottom view of the locking wing of FIG. 7A.
Figure 7A:
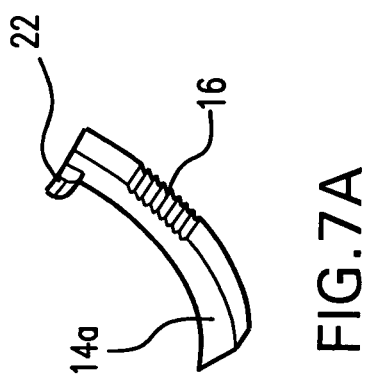
FIG. 7A is a detailed perspective view of a locking wing of the interspinous implant of FIG. 1.

Each locking wing 14a-14d includes a set of ratchet teeth 16, as best seen in FIGS. 7A-7C. The ratchet teeth 16 on each wing 14a-14d are dimensioned and configured to engage a corresponding pawl structure 18 formed adjacent the openings 46a-46d on the shell 12 during deployment, so as to lock the wings 14a-14d in the desired position. The locking wings 14a-14d fixate the adjacent spinous processes. While the implant 10 is used primarily as a spacer between spinous processes, the selectively deployable wings 14a-14d enable the implant 10 to be used to distract the spinous process as well. Advantageously, once the wings 14a-14d are deployed to fixate the spinous processes, migration of the implant 10 is prevented.

As best seen in FIG. 3, the two wings 14c and 14b on the side of the implant 10 are located on parallel, spaced apart geometric planes that extend on the side of the horizontal centerline of the implant shell 12. In other words, in a deployed position, locking wing 14b resides in a deployment plane that is parallel to the deployment plane of locking wing 14c. Similarly, locking wing 14a resides in a plane that is parallel to the deployment plane of locking wing 14d. It follows that, locking wings 14a and 14c reside in a common deployment plane, and locking wings 14b and 14d reside in a common deployment plane. This orientation helps to prevent migration of the device and maintain stability within the spinous process.

The movement or deployment of the locking wings 14a-14d is controlled or otherwise effectuated by a pair of coaxial locking wheels 20a and 20b, shown in FIGS. 4 and 8A-8D. The locking wheels 20a and 20b have a central opening 25a and 25b, respectively, for mounting on a central hub 21 in the shell 12. Locking wheel 20a nestles in upper shell portion 12a to control the movement of wings 14a and 14c, while locking wheel 20b nestles in lower shell portion 12b to control the movement of wings 14b and 14d. More particularly, each of the opposed ends 23a, 23b of locking wheels 20a, 20b are adapted and configured to exert a force against a bearing surface 22 formed at the end of each locking wing 14a-14d, which is best seen in FIGS. 10A and 10B.

In accordance with a preferred embodiment of the subject invention, the locking wheels 20a, 20b and thus the locking wings 14a-14d are controlled by a deployment cable 27, shown in FIG. 10B. One or more cables may be employed. The deployment cable 27 attaches to a key-shaped opening 41 formed in the locking wheels 20a, 20b to facilitate remote actuation of the locking wheels 20a, 20b and corresponding movement of the ratcheting locking wings 14a, 14b. The cable 27 splits on the distal end and terminates in two balls (not shown). Each ball can pass through the respective key-shaped opening 41 and be selectively captured therein. The cable 27 passes out of the shell 12 via a passage 90 for use by the surgeon. Once deployed, the cable 27 may be disengaged from the key-shaped opening 41 or cut as described below.

Alternatively, the key-shaped opening 41 may be located further from the pivot point of the locking wheels 20a, 20b to provide a greater mechanical advantage. The cable 27 may also form a loop by attaching to the two key-shaped openings 41. The loop may be a simple loop at the distal end of the cable 27 or a long loop that passes out of the shell via passage 90. Additionally, a similar second loop of cable (not shown) might attach to two other key-shaped openings on the opposite ends of the locking wheels 20a, 20b to further increase the mechanical force during deployment. The second loop of cable would also pass out of the implant 10 through a passage similar to passage 90 but formed in the distal end of the implant 10. Once deployed, the cable loop may either be cut or left as part of the implant 10.

As best seen in FIGS. 1-3, 9A-9D and 11, the interspinous implant 10 is associated with a placement tool 24 adapted and configured to facilitate the percutaneous introduction of the implant 10. Placement tool 24 includes an elongated tubular stem 26 having a straightened distal portion 26a and a curved proximal portion 26b. In another embodiment, the tubular stem 26 may be curved without a straightened portion. The tubular stem 26 has a central lumen 29 for accommodating the proximal portion of the deployment cable 27. At a distal end, the placement tool 24 has a coupling sleeve 28 for selectively engaging a locking cuff 49 on a tail 10b of the shell 12. The sleeve 28 has a slot 92 and the cuff 49 has one or more protrusions 94 that engage to form a twist lock to selectively couple the placement tool 24 to the shell 12. The sleeve 28 may also form a cutting surface 51, as best seen in FIGS. 10A and 10B, against which the cable 27 may be routed for cutting. As the sleeve 28 rotates, a protrusion 59 lifts the cable 27 so that the cutting surface 51 can sever the cable 27 after the locking wings 14a-14d have been deployed by the locking wheels 20a, 20b. When the cable 27 is a long loop, one end is simply released while the other end of the cable 27 is pulled to remove the cable 27. It is also envisioned that each locking wheel 20a, 20b may have a loop or respective cable 27. In still another embodiment, the cable 27 is relatively short and remains attached to the locking wheels 20a, 20b after deployment. To actuate the locking wheels 20a, 20b, there is a secondary longer cable (not shown) that passes from the proximal to the distal end of the placement tool 24 and loops around the cable 27. The secondary cable then passes back out of the proximal end of the placement tool 24. The ends of the secondary cable are pulled in order to pull cable 27 and, in turn, actuate the locking wheels 20a, 20b. Then, one end of the secondary cable is simply released, while the other end is pulled to remove the secondary cable.

Figure 8E:
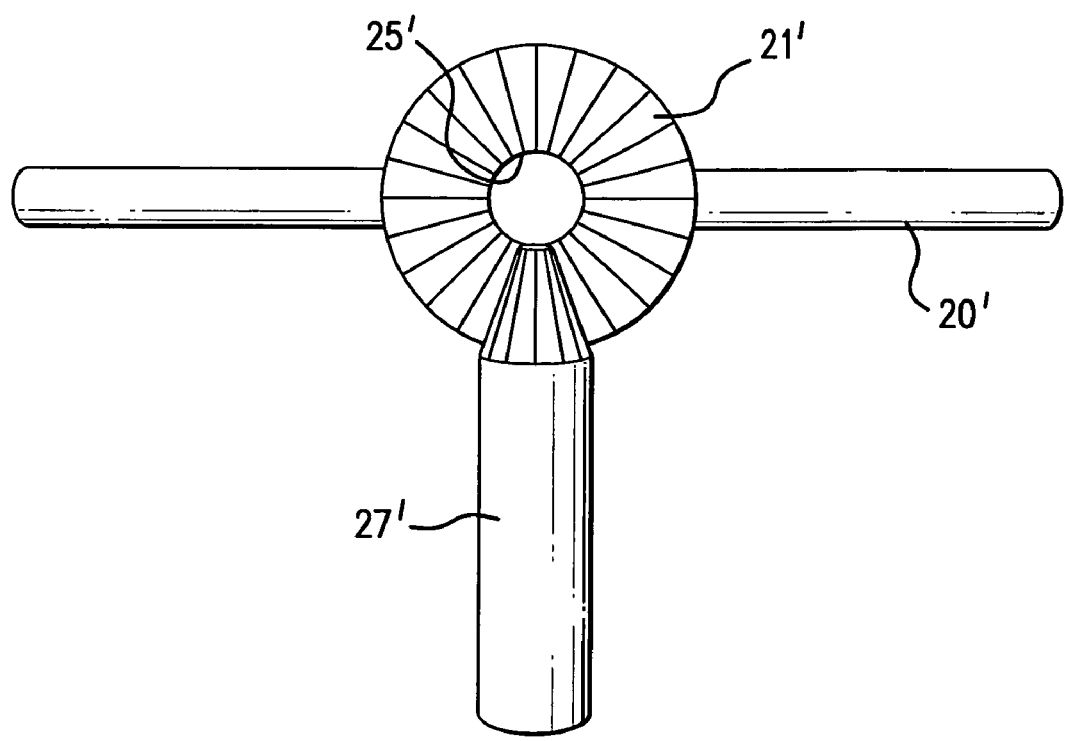
FIG. 8E is a detailed top view of another locking wheel and a portion of the actuating mechanism for use in the interspinous implant of FIG. 1.

Referring to FIG. 8E, another embodiment of a locking wheel 20' is shown. The locking wheel 20' has spaced grooves located on the central hub 21' adapted and configured to engage complementary spaced teeth on an actuating mechanism 27'. The central hub 21' is relatively thicker near the central opening 25' so that the teeth on the conical head of the actuating mechanism 27' effectively interdigitate with the grooves to form a gear drive mechanism. Various other shapes could also form an effective gear drive mechanism. The actuating mechanism 27' is preferably a rod that extends along the long axis of the implant 10. The conical head of the actuating device 27' may be between the two locking wheels 20' or each locking wheel may have a respective actuating mechanism 27'. On the other end (not shown), the actuating mechanism 27' terminates near the end of the shell 12 and forms a slot. A screwdriver type of device (not shown) would insert down the placement tool 24 and couple to the rod slot. By turning the screwdriver type device, the actuating mechanism 27' would turn and, thereby, one or both of the locking wheels 20' would turn in opposite direction to accomplish deployment of the locking wings 14a, 14b of the implant 10.

Stylet Assembly

Figure 12:
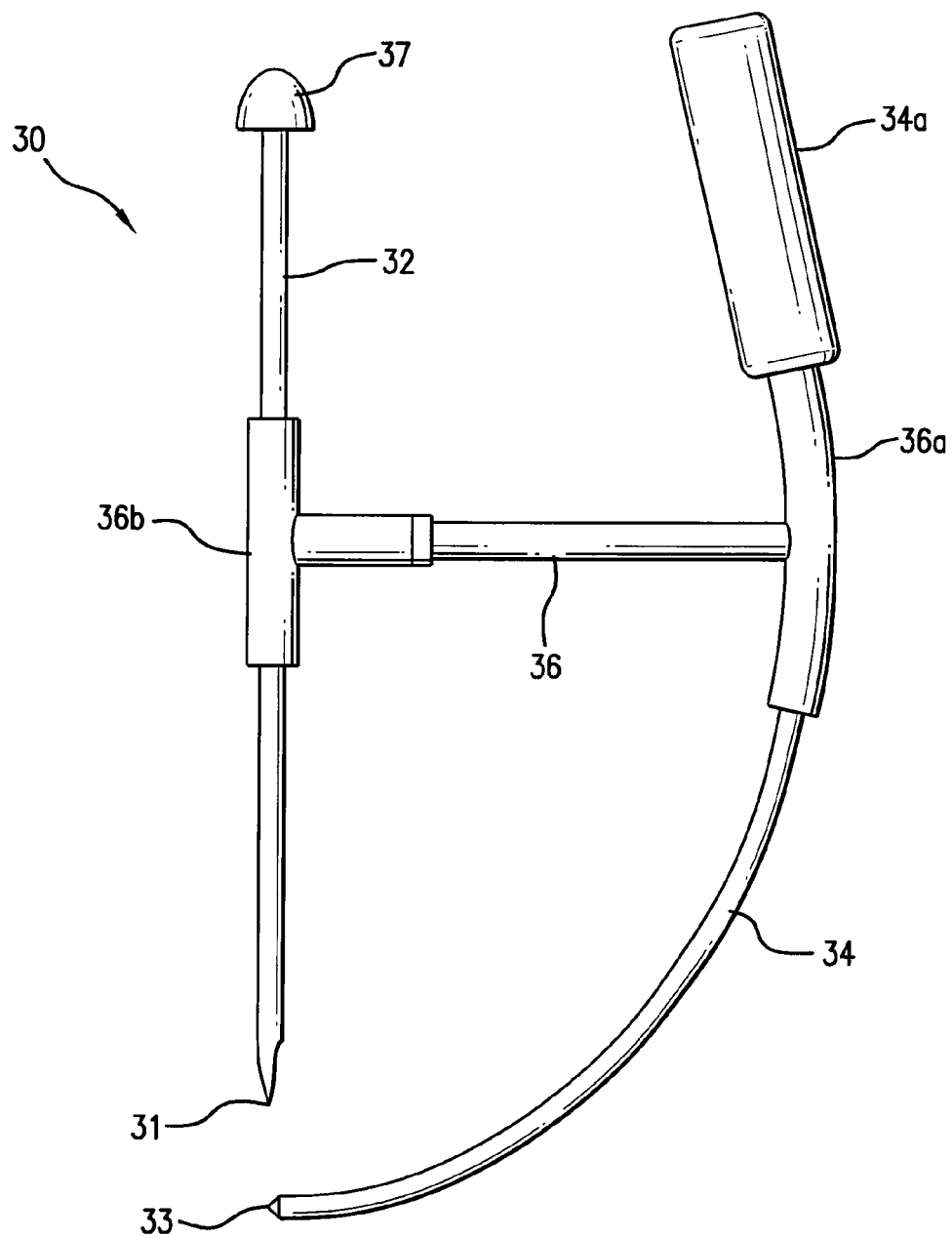
FIG. 12 is an elevational view of the stylet assembly used to percutaneously deploy the interspinous implant of the subject invention.

Referring now to FIG. 12, there is shown a stylet assembly 30 adapted and configured to facilitate the percutaneous insertion of the interspinous implant 10. The stylet assembly 30 includes an elongated graduated positioning stylet 32 for setting the position of the assembly 30 over the central axis of the patient's spine. On a distal end, the graduated positioning stylet 32 has a pointed tip 31 adapted and configured to be inserted in the patient. On a proximal end, the graduated positioning stylet 32 has a knob 37 to allow a surgeon to more easily control the stylet 32. The stylet assembly 30 further includes a curved stylet 34 for gaining lateral access to the interspinous space and an adjustable guide bridge 36 having a curved guide sleeve 36a for the curved stylet 34. The adjustable guide bridge 36 also has a central portion 36b to act as an insertion guide for the graduated positioning stylet 32. The curved stylet 34 has a distal end 33 adapted and configured to be inserted in the patient and a proximal end with a handle/travel stop 34a. The relationship between the handle/travel stop 34a and curved guide sleeve 36a sets a maximum insertion depth of the curved stylet 34.

Unilateral Placement of the Implant

Figure 13:
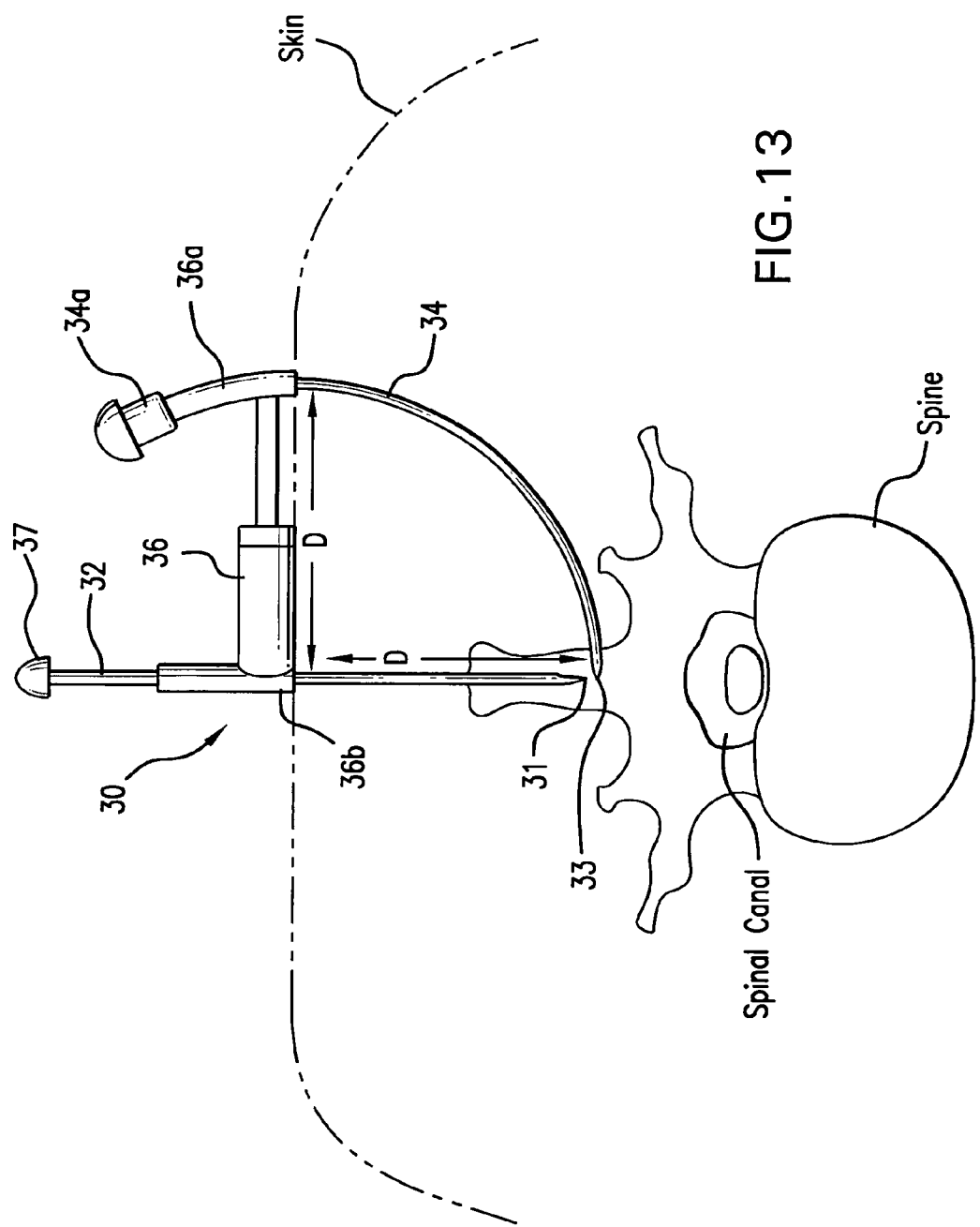
FIGS. 13 through 16 illustrate the percutaneous introduction of the interspinous implant of the subject invention by way of a unilateral approach from one side of the spine.

Referring to FIG. 13, in use the graduated stylet 32 is advanced through a small percutaneous incision in the patient's back, under fluoroscopy, so that the pointed tip 31 reaches to the interspinous space. The distance (D) from the skin to the interspinous space is then noted, based on graduations on the stylet 32. Alternatively, the same distance can be measured from a pre-operative CT scan. In each event, the center guide sleeve 36b of the adjustable guide bridge 36 is positioned over stylet 32, and the distance (D) is marked off in a direction perpendicular to the length of the spine. This distance (D) corresponds to the adjusted length of the adjustable guide bridge 36 of stylet assembly 30. Thereafter, the curved stylet 34 is advanced down to the interspinous space through the curved guide sleeve 36a of the adjustable guide bridge 36. The curved stylet 34 has a radius of curvature equal to D so that upon insertion, the distal end 33 moves adjacent the pointed tip 31 of the graduated stylet 32 at the interspinous space. At this point of advancement of the curved stylet 34, the travel stop 34a at the end of the stylet 34 abuts the guide sleeve 36a to prevent further extension. Thereupon, the travel stop 34a is threadably or otherwise removed from the end of the curved stylet 34, and the remainder of the stylet assembly 30 including the graduated stylet 32 are removed as well. However, the curved stylet 34 remains in place as shown in FIG. 14.

Figure 14:
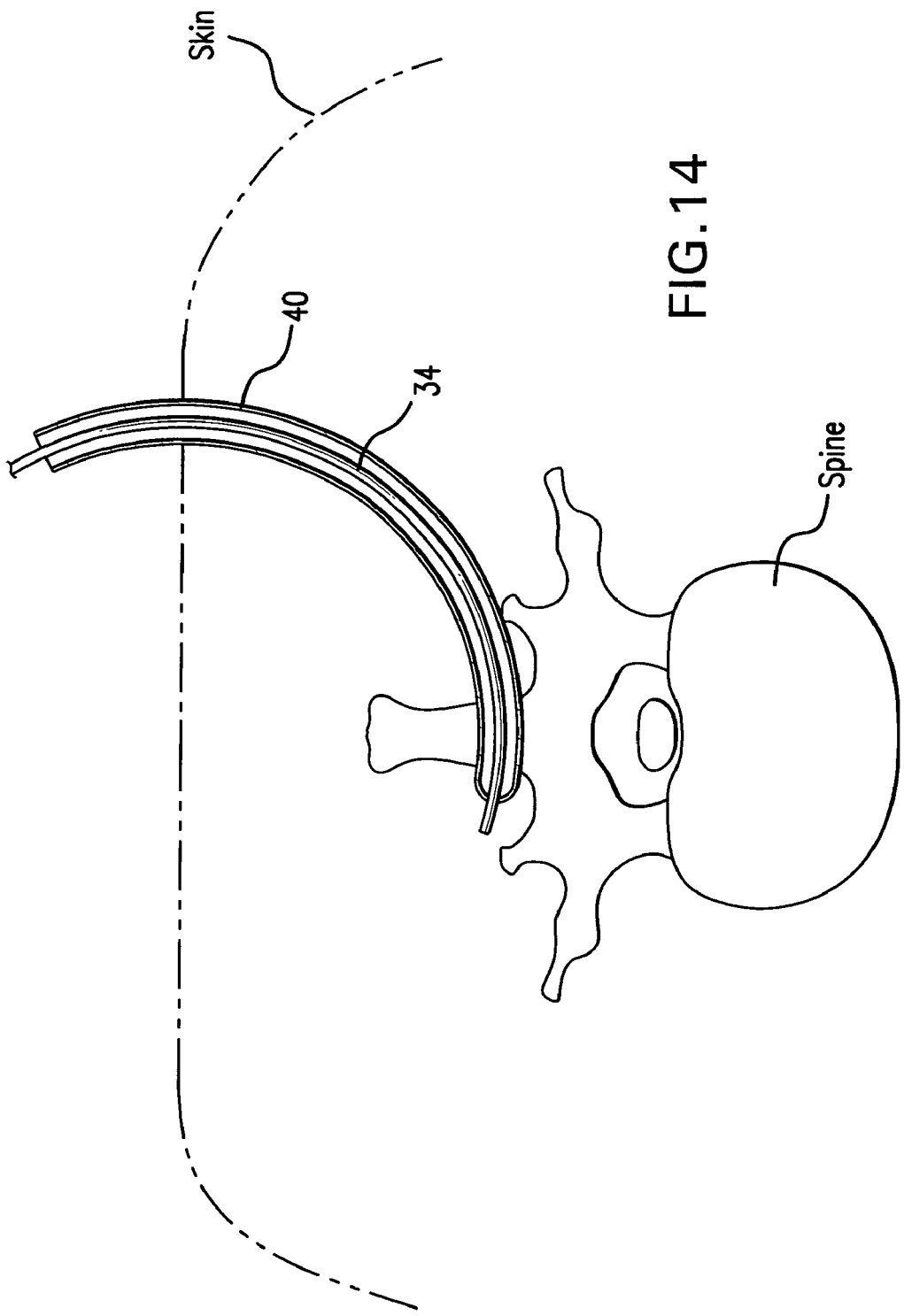
Figure 15:
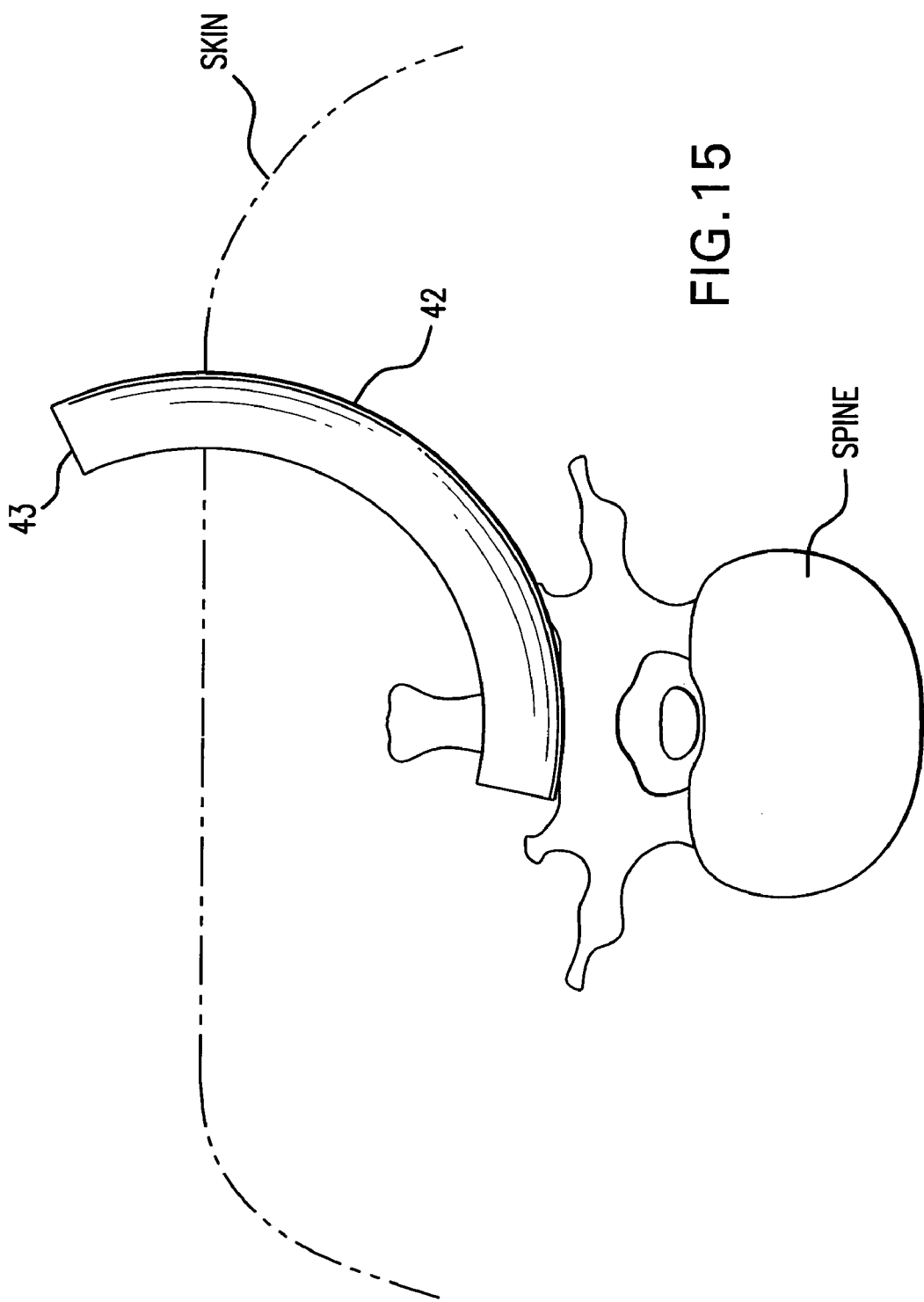

Then, as shown in FIGS. 14 and 15, successive dilators 40, 42 are placed over the curved stylet 34, while observing the interspinous space under fluoroscopy. The dilators 40, 42 also may have radii of curvature equal to D. The dilators 40, 42 serve to distract the interspinous space. Although two dilators 40, 42 are shown, more or less could be utilized to accomplish the desired distraction of the interspinous space. Once the adequate distraction of the interspinous space is observed, the implant 10 is percutaneously inserted through a lumen 43 formed in the last dilator 42. Preferably, the dilators 40, 42 distract the spinous processed and the implant 10 only maintains the distraction although the implant 10 may also perform distraction. Alternatively, the deployment of the implant 10 may be done by threading the implant 10 over the curved stylet 34 as a guide into the interspinous space by way of the guide bore 15 on the lower shell portion 12b.

Figure 16:
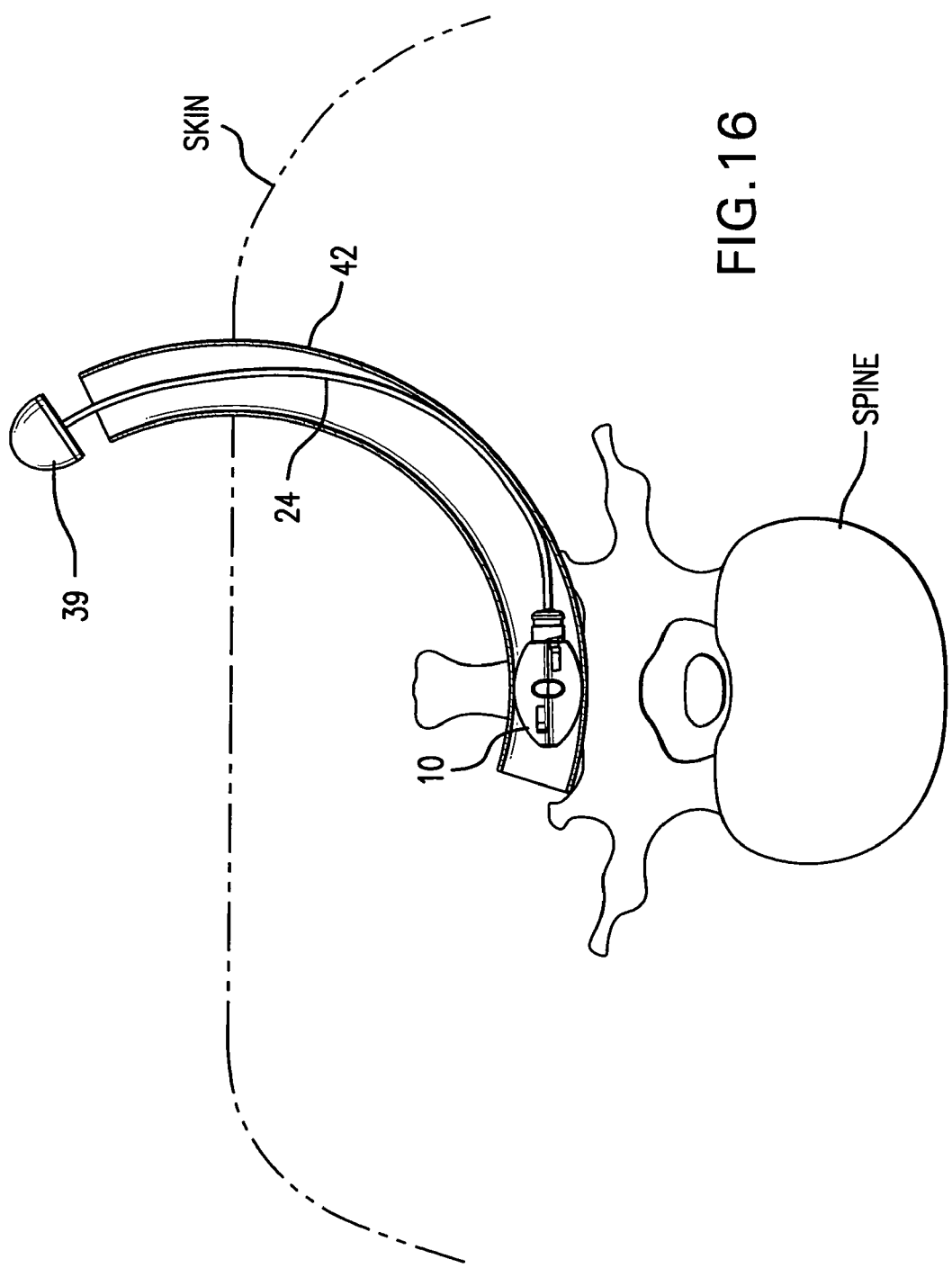

The implant 10 is maneuvered down to the interspinous space. As shown in FIG. 16, the implant 10 has a knob 39 selectively attached to the placement tool 24 to help the physician maneuver the implant 10. The knob 39 may include an extension that inserts into the central lumen 29 in order to make the stem 26 more rigid. Once the implant 10 is in position, the dilator 42 may be removed, while maintaining the position of the implant 10 for subsequent deployment of the locking wings 14a-14b.

Actuating the Locking Wings after Unilateral Insertion

Once the shell 12 is nestled between the spinous processes so that contact is made with the bone at the depressions 13, the locking wings 14a-14d are deployed. The surgeon utilizes the cable 27 to deploy the locking wings 14a-14d and, thereby, fix the position of the implant 10. The distal end 27a, 27b of the cable 27 is attached to the coaxial locking wheels 20a, 20b, respectively, so that as the cable 27 is pulled proximally, the locking wheels 20a, 20b rotate about the central hub 21 in the shell 12.

The opposing ends 23a, 23b of the locking wheels 20a, 20b push against the bearing surfaces 22 of the respective locking wings 14a-14d so that the locking wings 14a-14d are urged outward in the guide tracks 19 of the shell 12. As the ratchet teeth 16 of the locking wings 14a-14d move outward past the pawl structure 18 of the shell 12, the pawl 18 engages the corresponding ratchet tooth 16 to prevent the locking wings 14a-14d from moving inward back into the shell 12. As a result of the outward movement, the locking wings 14a-14d engage the spinous processes until the surgeon feels adequate resistance, e.g., deployment. Once the locking wings 14a-14d are deployed, the cable 27 is released or cut. The implant 10 then remains deployed between the spinous processes. In one embodiment, a biasing element or elements such as a spring extends between the locking wheels 20a, 20b so that movement thereof does not occur before or after deployment.

In one embodiment, to release the cable 27, a second cable (not shown) extends down the placement tool 24. The second cable loops around the cable 27 and returns through the central lumen 29 of the placement tool 24. The surgeon can pull on the second cable to effect a pull on cable 27. Once the locking wings are deployed, the surgeon releases one end of the second cable loop, and then pulls this second cable out of the placement tool 24, thus leaving cable 27 with the implant in the patient.

Bilateral Placement of the Implant

Figure 17:
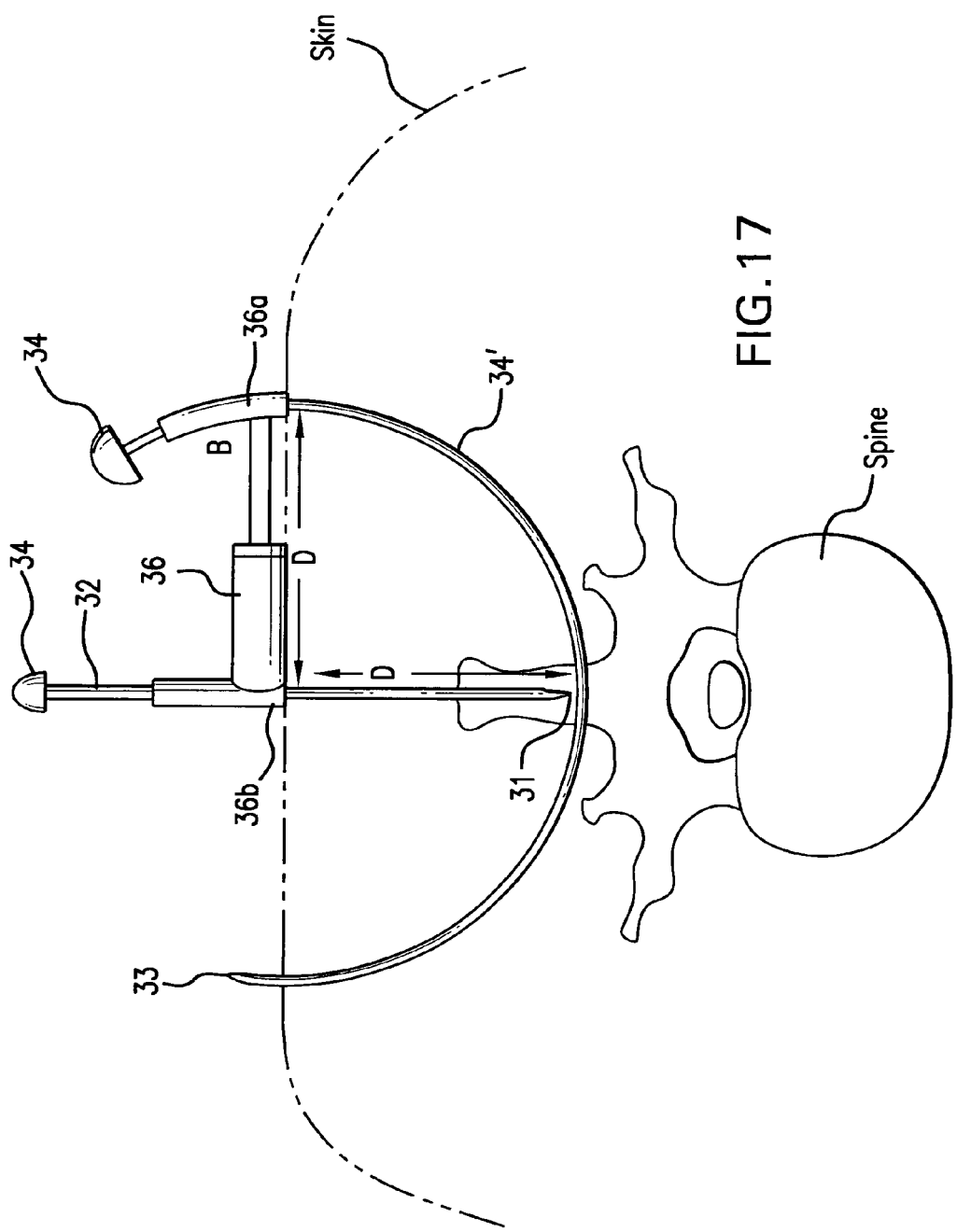
FIGS. 17 through 21 illustrate the percutaneous introduction of the interspinous implant of the subject invention by way of a bilateral approach from either side of the spine.

Referring to FIGS. 17-21, there are illustrated the operative steps used in the bilateral placement of the interspinous implant 10 of the subject invention. First, as shown in FIG. 17, the central portion 36b of the adjustable guide bridge 36 is positioned over the graduated stylet 32, and the graduated stylet 32 is inserted to the depth of the patient's spine. The measured distance (D) is used to size the adjustable guide bridge 36. A second curved stylet 34', similar to curved stylet 34 but longer, is then advanced through the skin down to the interspinous space through the curved guide sleeve 36a of the adjustable guide bridge 36. The curved stylet 34' is also extendable, and the advancement of the curved stylet 34' continues until the distal end 33 of the curved stylet 34' punctures the skin on the opposite side of the spine.

Figure 18:
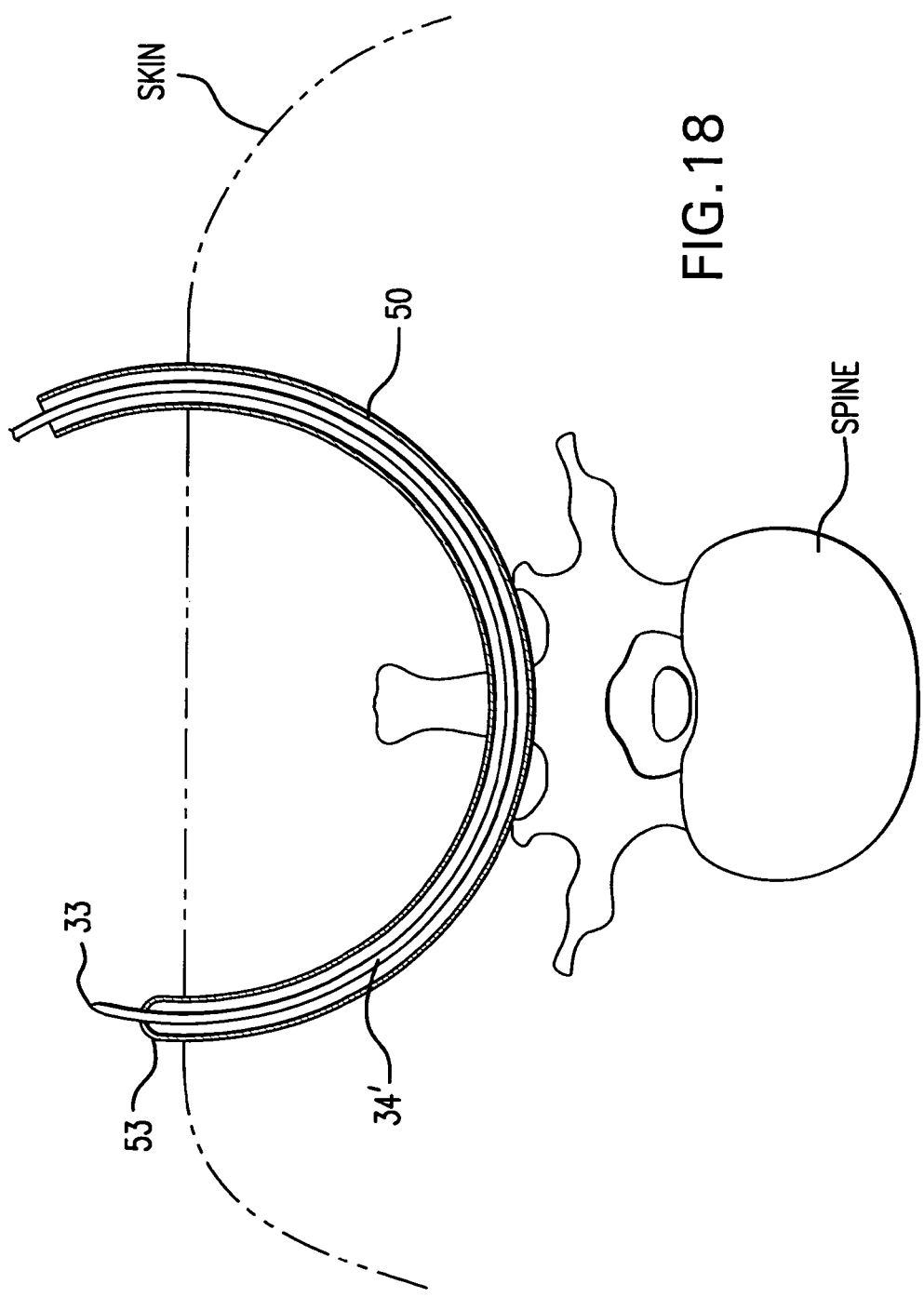
Figure 19:
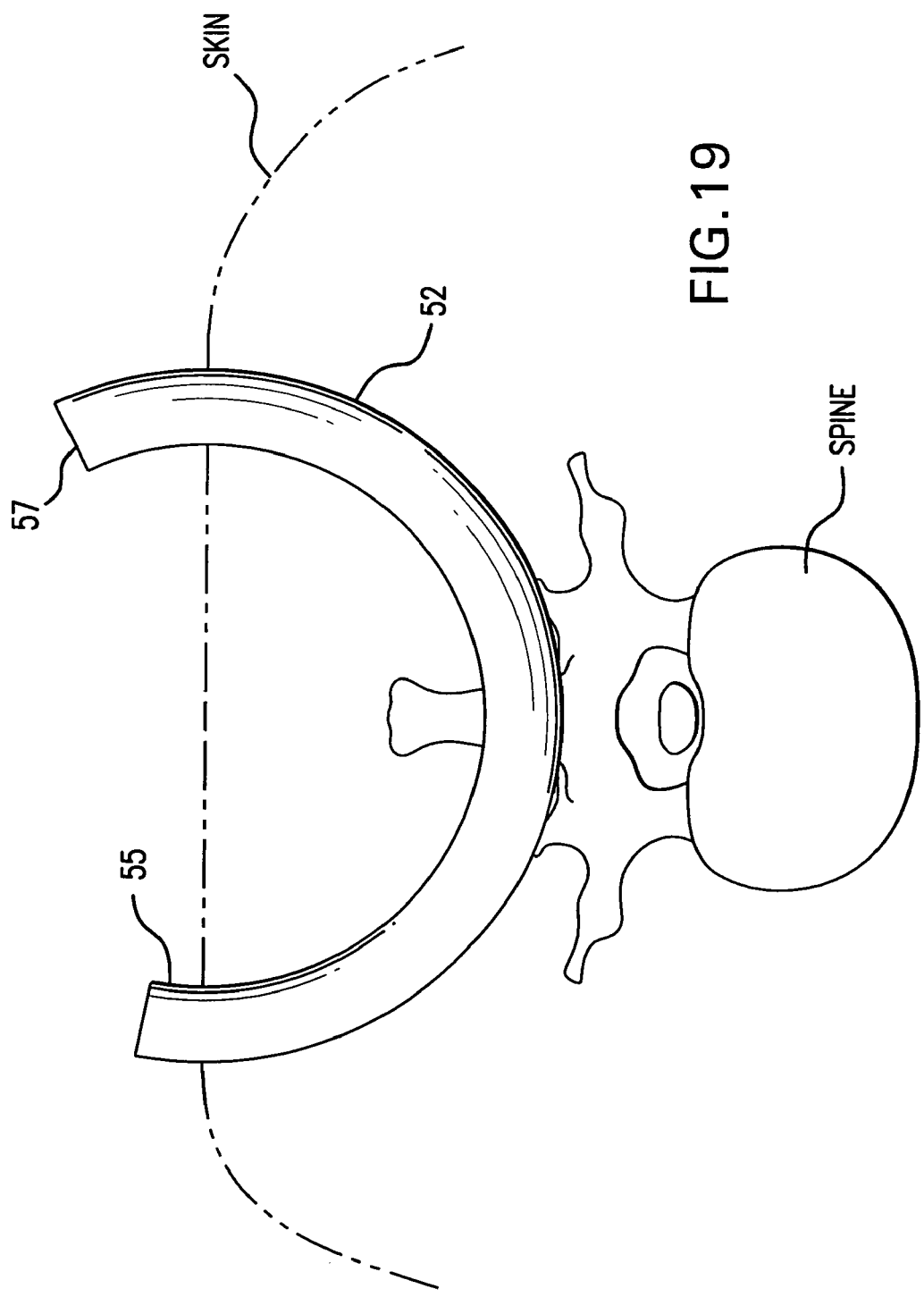

As shown in FIGS. 18 and 19, the adjustable guide bridge 36 and graduated stylet 32 are removed. Successive tubular dilators 50, 52 are placed over the curved stylet 34' while observing the interspinous space under fluoroscopy. These dilators 50, 52, with successively larger diameters, are along the same route as the curved stylet 34' through the interspinous space until distal ends 53, 55 respectively, pass out of the patient's body.

Figure 20:
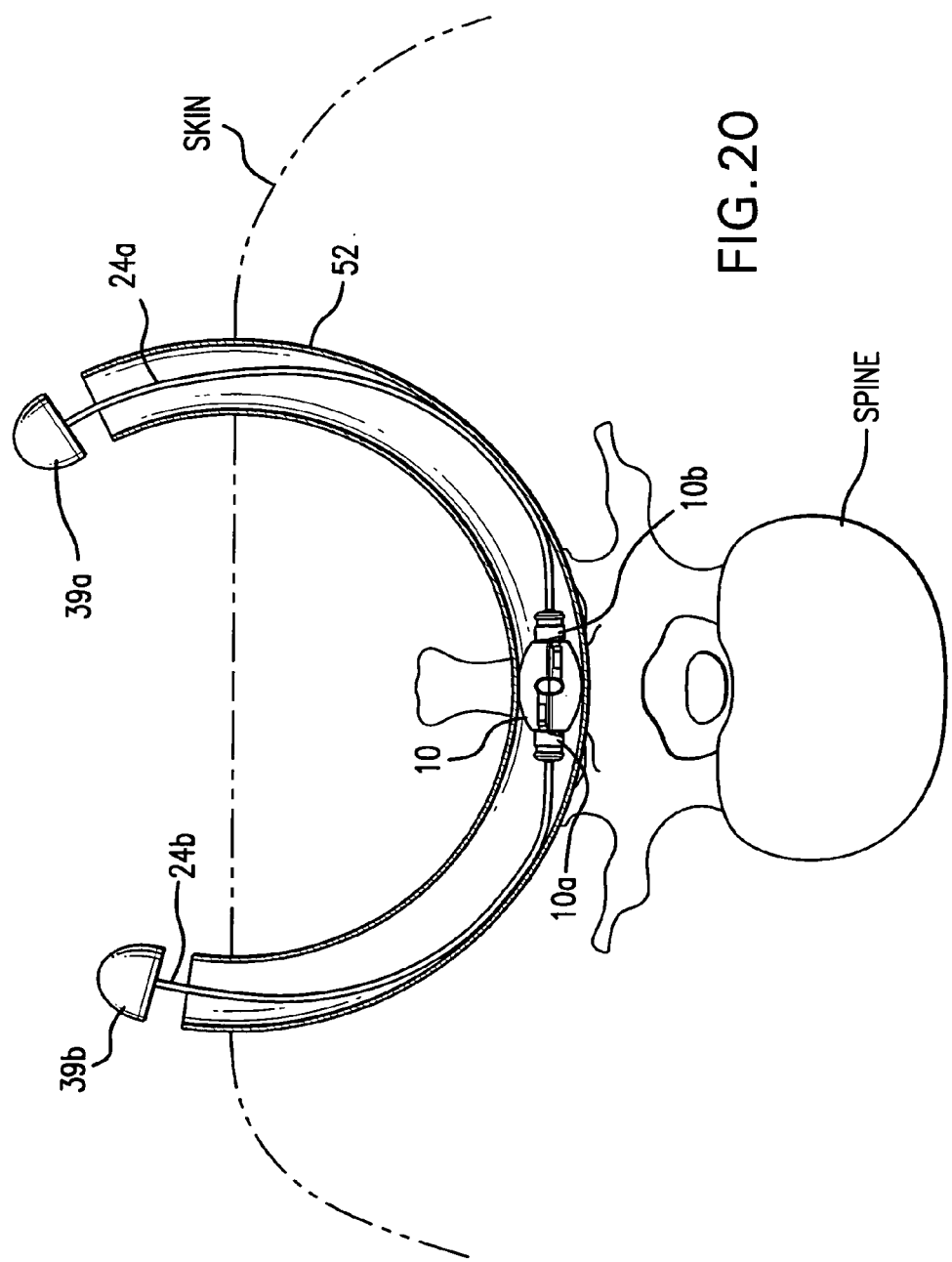

Once adequate distraction of the interspinous space is observed, the interspinous implant 10, with a profile slightly less than the diameter of the larger dilator 52, is percutaneously inserted through the lumen 57 of the last dilator 55. The surgeon guides the implant 10 down to the interspinous space, approaching from either or both sides of the spine, as shown in FIG. 20. Alternatively, once the interspinous space has been adequately distracted by the dilators 50, 52, a stylet guide (not shown) could again be inserted after removal of the last dilator 52. The implant 10 could then be inserted over the stylet guide into the interspinous space.

Actuating the Locking Wings after Bilateral Insertion

As best seen in FIG. 20, to actuate the locking wings 14a-14d, the implant is inserted through the final dilator 52 using the placement tool 24a attached to the proximal tail 10b of the implant 10. By passing a second placement tool 24b into the dilator 52 in an opposing direction, the second placement tool 24b attaches to a distal nose 10a of the implant 10. Each placement tool 24a, 24b has a corresponding knob 39a, 39a on the proximal end. The final dilator 52 is fully or partially removed while maintaining the position of the implant 10 with the placement tool 24a or tools 24a, 24b, as the case may be.

Figure 21:
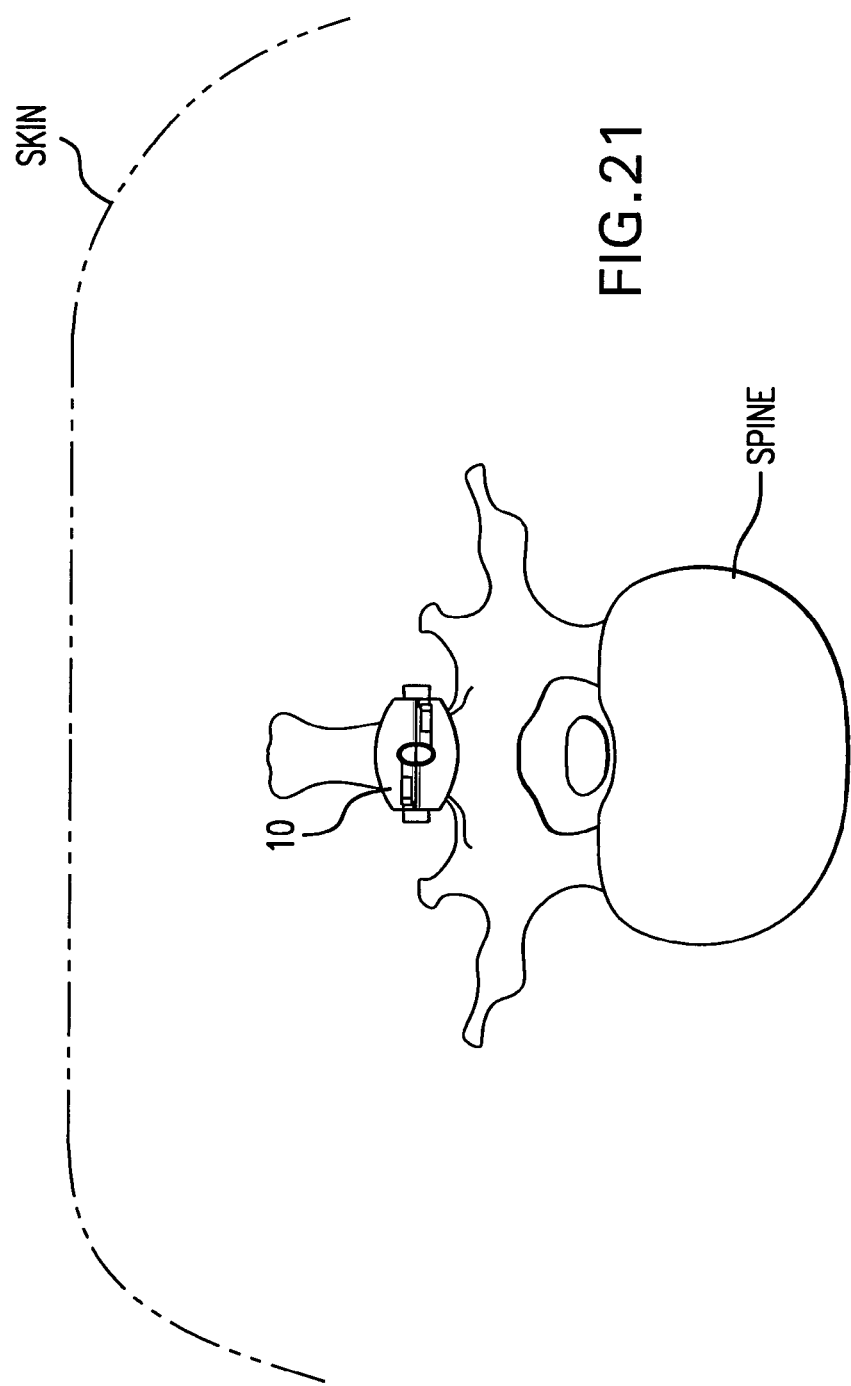

While holding the implant 10 in position with the placement tools 24a, 24b, the deployment cable (not shown) is pulled to actuate the locking wings 14a-14d of implant 10. A distal end of the cable is attached to the coaxial locking wheels 20a, 20b so that as the cable is pulled, the locking wheels 20a, 20b rotate about the central hub 21 in the shell 12. The opposing ends 23a, 23b of the locking wheels 20a, 20b push against the bearing surfaces 22 of the respective locking wings 14a-14d so that the locking wings 14a-14d slide outward in the guide tracks 19 of the shell 12. As the ratchet teeth 16 of the locking wings 14a-14d move outward past the pawl structure 18 of the shell, the pawl 18 engages the corresponding ratchet tooth 16 to prevent the locking wings 14a-14d from moving inward back into the shell 12. As a result of the outward movement, the locking wings 14a-14d engage the spinous processes until the surgeon feels adequate resistance, e.g., deployment as shown in FIG. 21.

Once the locking wings 14a-14d are deployed, the cable is released and the placement tools 24a, 24b are detached from the nose 10a and tail 10b of the implant 10. The implant 10 then remains deployed between the spinous processes, as shown in FIG. 21. Before fully detaching the placement tool 24a from the implant 10, the deployment cable is cut. To cut the cable, the placement tool 24a rotates the cutting surface 51 and, in turn, the cable is severed by being routed against the cutting surface 51.

It is envisioned that the placement tools 24a, 24b each attach to the interspinous implant 10 through a selective twist lock as noted above. Alternatively, the placement tools 24a, 24b could be designed to also have tapered ends with prongs that attach to a bulbous portion of the nose 10a and tail 10b of the interspinous implant 10. Similarly, an unlocking rod could be inserted into the placement tools 24a, 24b or dilator 52 to disengage them from the shell 12.

Alternative Control Device

Figure 22:
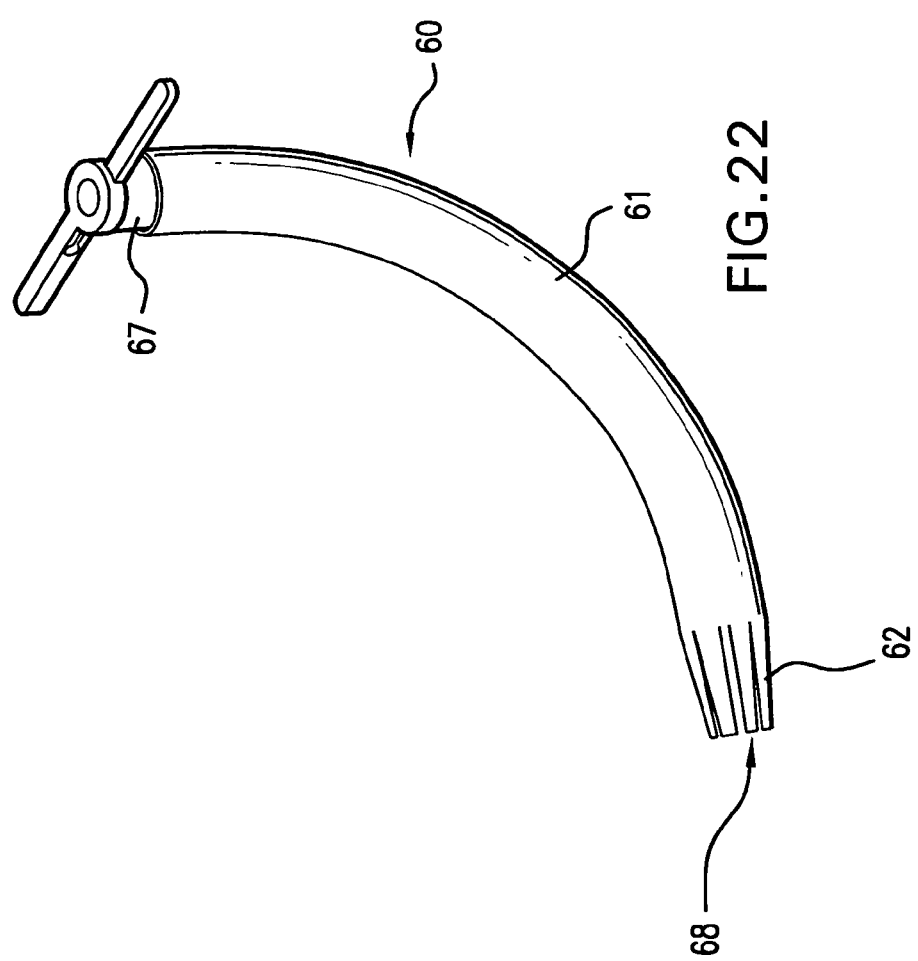
FIG. 22 is a perspective view of a placement or cable attachment device utilized in conjunction with the interspinous implant of the subject invention.
Figure 23:
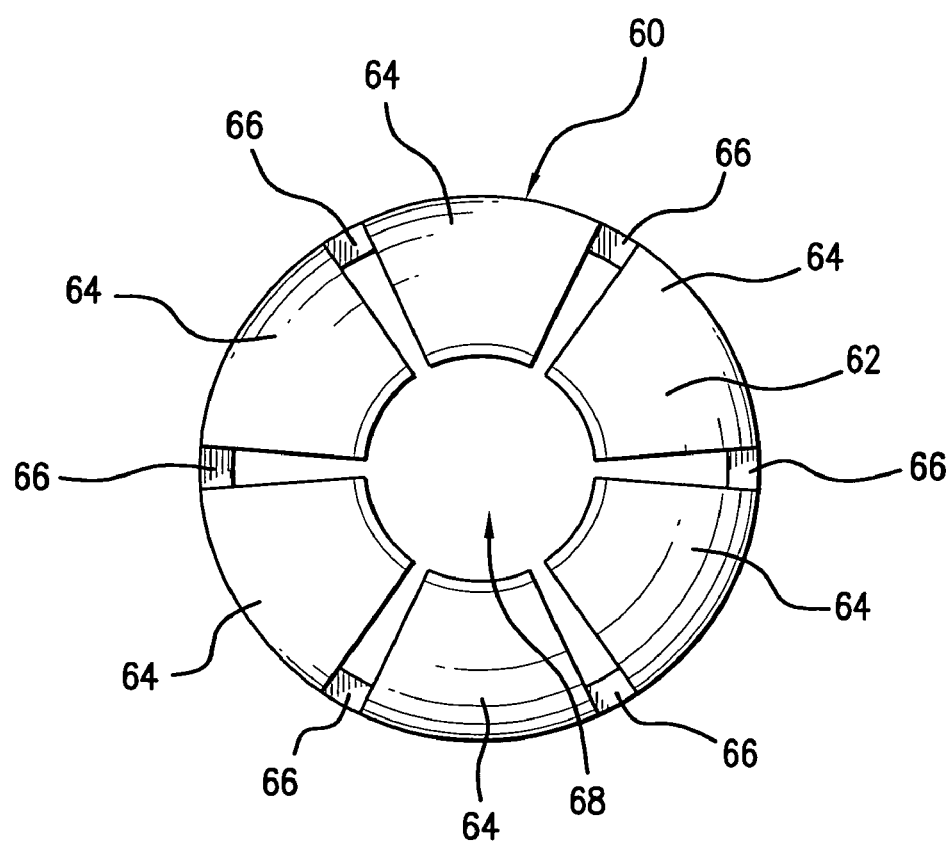
FIG. 23 is a distal end view of the attachment device of FIG. 22.

Referring now to FIGS. 22 and 23, a control device 60 is shown. The control device 60 may be used to actuate the cable(s) 27 or to place the implant 10. Accordingly, the size and shape may vary significantly from that shown because the principle of operation is widely applicable. The control device 60 has an arcuate tube 61. Preferably, the arcuate tube 61 has a radius of curvature of D.

The control device 60 may be used to actuate the cable 27 so that cutting is not required by detaching from the cable 27 after deployment. For example, the arcuate tube 61 has a tapered distal end 62. The tapered end 62 has radially inwardly extending flexible prongs 64 with longitudinal slots 66 in between. The prongs 64 form a distal opening 68. It is envisioned that the proximal end of the deployment cable 27 would be attached to a small ball (not shown) on the proximal end of the cable 27. The ball would have a diameter slightly greater than the opening 68 so that the ball is captured in the tapered distal end 62. In particular, the flexible prongs 64 of the cable attachment device 60 capture the cable ball. By capturing the cable ball, the control device 60 can be used to pull the cable 27 by pulling the device 60.

Once the cable 27 has been pulled, with the deployment of the locking wings 14a-14d of the implant 10, the ball of the cable 27 is released from the tapered distal end 62 of the arcuate tube 61. Release of the ball from the control device 60 is accomplished by inserting a second tube 67 into the arcuate tube 61, as shown in FIG. 22. The second tube 67 would have a slightly smaller diameter than the arcuate tube 61. The tube 67 provides adequate force to deflect the prongs 64 resulting in an increase in diameter of the opening 68 and, in turn, release of the ball on the end of the deployment cable 27. Thus, a predetermined, short amount of cable 27 may be left implanted.

It is also envisioned that the implant 10 could be designed so that deployment of the wings 14a-14d is accomplished from the nose 10a and tail 10b of the shell 12, bilaterally, whereby two separate cables could be used to deploy the wings 14a-14d, doubling the mechanical advantage provided during a unilateral approach using a single deployment cable 27. The control device 60 may be used with one or both such cables.

In another embodiment, the control device 60 is used to place the implant 10. The flexible prongs 64 would attach to indentations on the implant 10. Two control devices 60 could be used with one attaching to each end of the implant 10. Thus, the arcuate tubes 61 could be used to position the implant 10. Upon deployment of the locking wings 14a-14d, second tubes 67 would be used to release the control devices 60 from the implant 10.

Using the Locking Wings to Distract

In an alternative approach, the locking wings 14a-14d are used to distract the spinous process. Rather than inserting increasing diameter dilators, the implant 10 is put in position. Then, the cable 27 is used to not only deploy the locking wings 14a-14d but the locking wings 14a-14d are also sized and configured to engage and distract the spinous process. For example, each locking wing 14a-14d may have a hook shaped protrusion positioned to distract the spine as the wings 14a-14d are deployed.

Implant in Deployed Position

Once deployed, the interspinous implant 10 of the subject invention is attached to the adjacent spinous processes. The implant 10 provides restriction of movement of the spine in both extension as well as flexion. With slight modification of the locking wings 14a-14d, however, the locking wings 14a-14d could alternatively be designed to simply abut the spinous processes, and thereby the implant 10 could allow flexion of the spine.

It is also envisioned that the implant 10 can permanently engage the spinous processes. For example, the tips of the locking wings 14a-14d can be sharp to create penetration of the spinous processes. The tips of the locking wings 14a-14d could be modified so that the edge that forms a point on opposing claws so that the opposing wings could penetrate deeper or through the spinous process bones. Further, the direction of the points on the opposing claws could be reversed. Additionally, the tips of the wings 14a-14d could have one or more barbs to prevent disengagement. Still further, the tips of the wings 14a-14d could have perforations that allow for bony in-growth from the spinous processes. In addition to being offset, preferably, the curves of the locking wings 14a-14d are slightly different to allow the opposing claims not to meet so that each can penetrate deeper through the bone.

Predetermining a Size of the Implant

Figure 24:
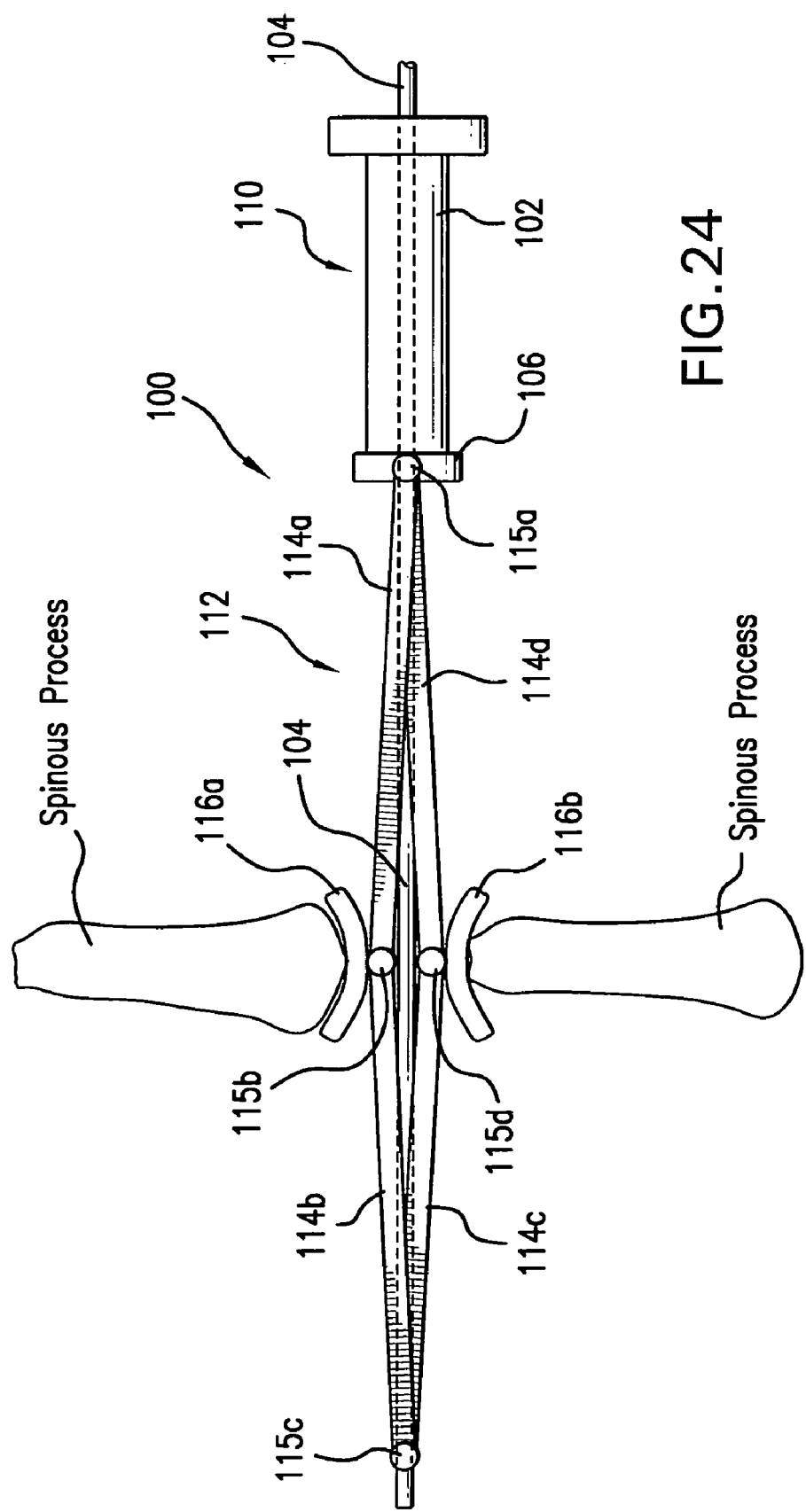
FIG. 24 is an illustration of an apparatus for measuring the optimum size of an interspinous implant, which is shown in an initial measuring position.
Figure 25:
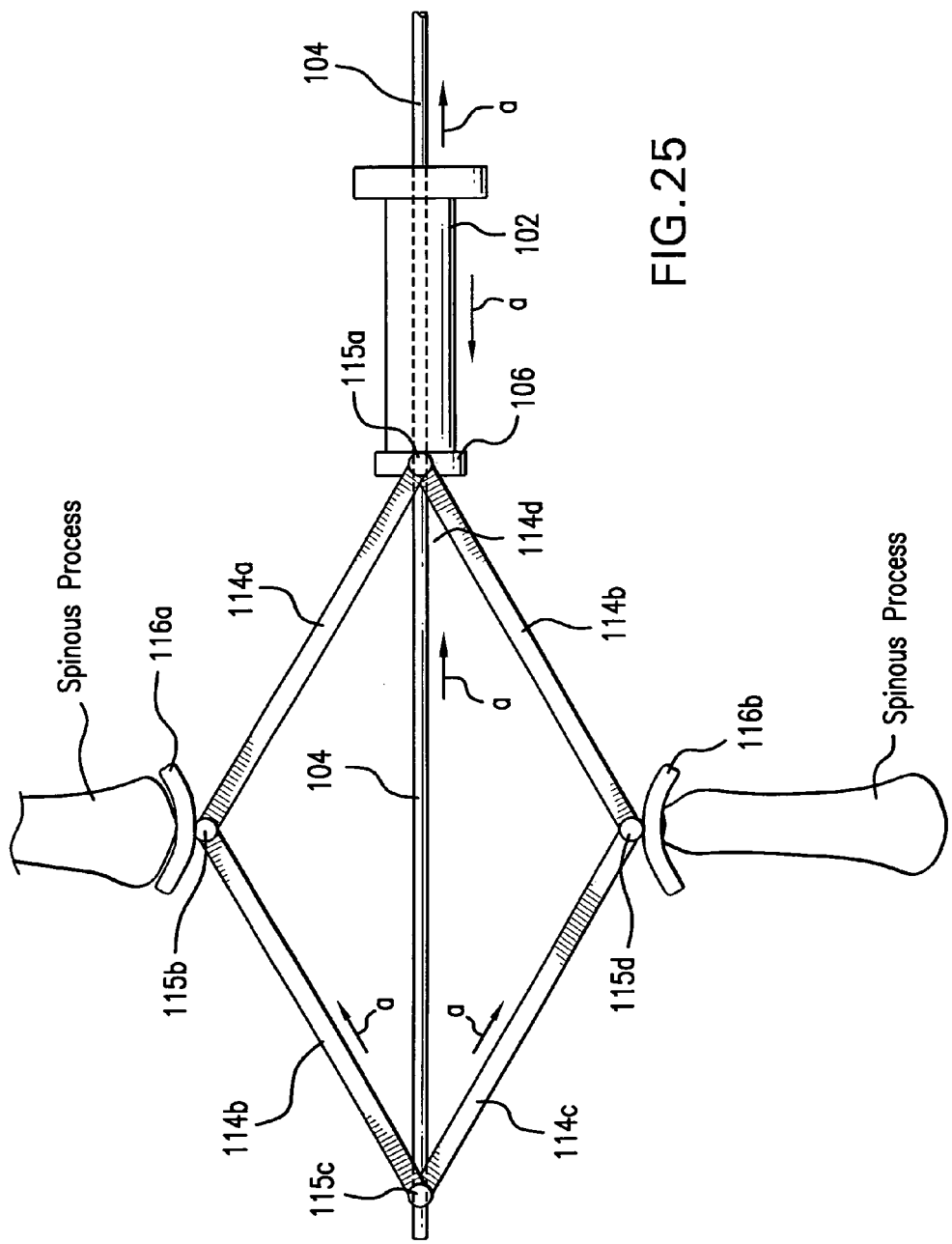
FIG. 25 is an illustration of the apparatus shown in FIG. 24 in an open or distracting position.

Referring now to FIGS. 24 and 25, there is shown an apparatus 100 and a method for measuring percutaneously the optimum size of an interspinous implant 10, which can range from about 8 mm in diameter to about 14 mm in diameter, depending upon the anatomy of the patient and the location of the implant 10 in the spinous process. Those skilled in the art will readily appreciate that the interspinous measurement devices disclosed herein can also be used to measure or otherwise determine an optimum degree of force for interspinous distraction.

Referring to FIG. 24, the measurement apparatus 100 is shown in a closed position, as the measurement apparatus 100 is percutaneously introduced into the interspinous space. The apparatus 100 includes a proximal deployment portion 110 that includes a plunger tube 102 carrying a rod 104. The rod 104 extends approximately flush with at the distal end 106 of the plunger tube 102.

The apparatus 100 further includes a distal measuring assembly 112, which consists of four connected arms 114a-114d. The connected arms 114a-114d are pivotally connected at four coupling joints 115a-115d. The rod 104 of the plunger tube 102 extends on the distal end to connect to the coupling joint 115c. Adjacent the coupling joints 115b, 115d, there are two opposed concave cradles 116a, 116b are adapted and configured to cup the adjacent spinous processes.

To measure percutaneously the optimum size of an interspinous implant 10, the apparatus 100 is placed so that the opposed concave cradles 116a, 116b are between adjacent spinous processes. The rod 104 is held stationary while the plunger tube 102 is pushed in a distal direction. The connected arms 114a-114d are driven to expand into a trapezoidal shape as shown by movement arrows "a" in FIG. 25). The expansion of the connected arms 114a-114d may cause the spinous processes to be distracted if not already done so by dilators. A measurement of the travel distance of rod 104 within in the tube 102 will correlate to the length to which the interspinous space was distracted, i.e., the size of the trapezoidal shape. Thus, the travel distance of the rod 104 can be used to determine the appropriate size of the interspinous implant 10. To facilitate measuring the travel distance, the rod 104 may have graduations or markings that correspond to an actual measurement or otherwise identify the appropriate size selection of the implant 10.

To measure the optimum degree of force for interspinous distraction, the plunger tube 102 and/or rod 104 are operatively associated with a strain gauge (not shown). Appropriate laboratory testing could be done to determine the optimal degree of distractive force so that the apparatus 100 is calibrated. The calibrated apparatus 100 could then be utilized to determine the appropriate implant 10 to apply that optimal force. To calibrate the apparatus 100, a clinical study could be performed where the amount of distractive force is correlated with radiological studies showing the degree of distraction. Further, clinical studies could be performed looking at long term clinical results, as well as possible subsidence of the implant 10 into the spinous processes, with different degrees of force exerted.

Figure 26:
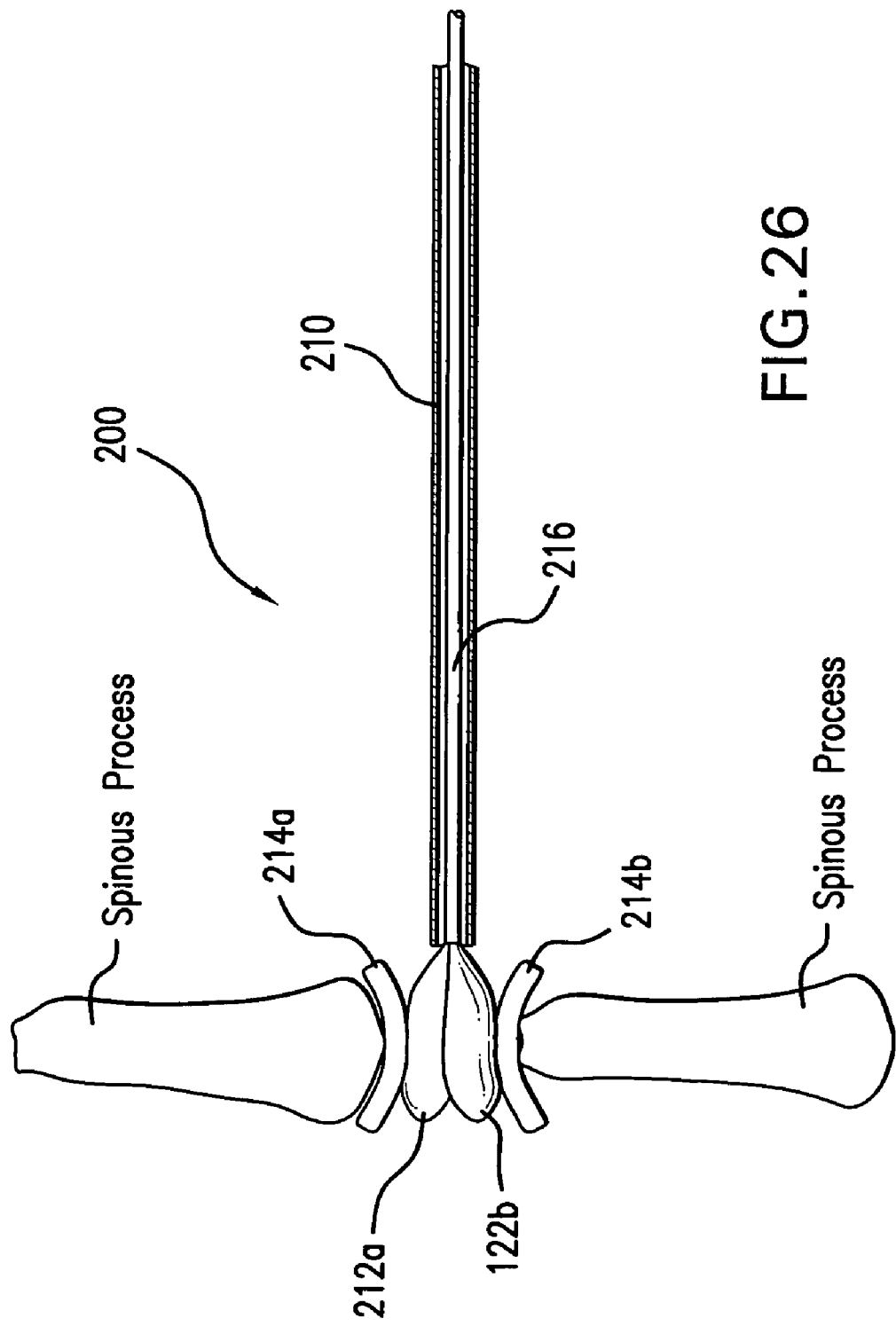
FIG. 26 is an illustration of another apparatus for measuring the optimum size of an interspinous implant, which is shown in an insertion or closed position.
Figure 27:
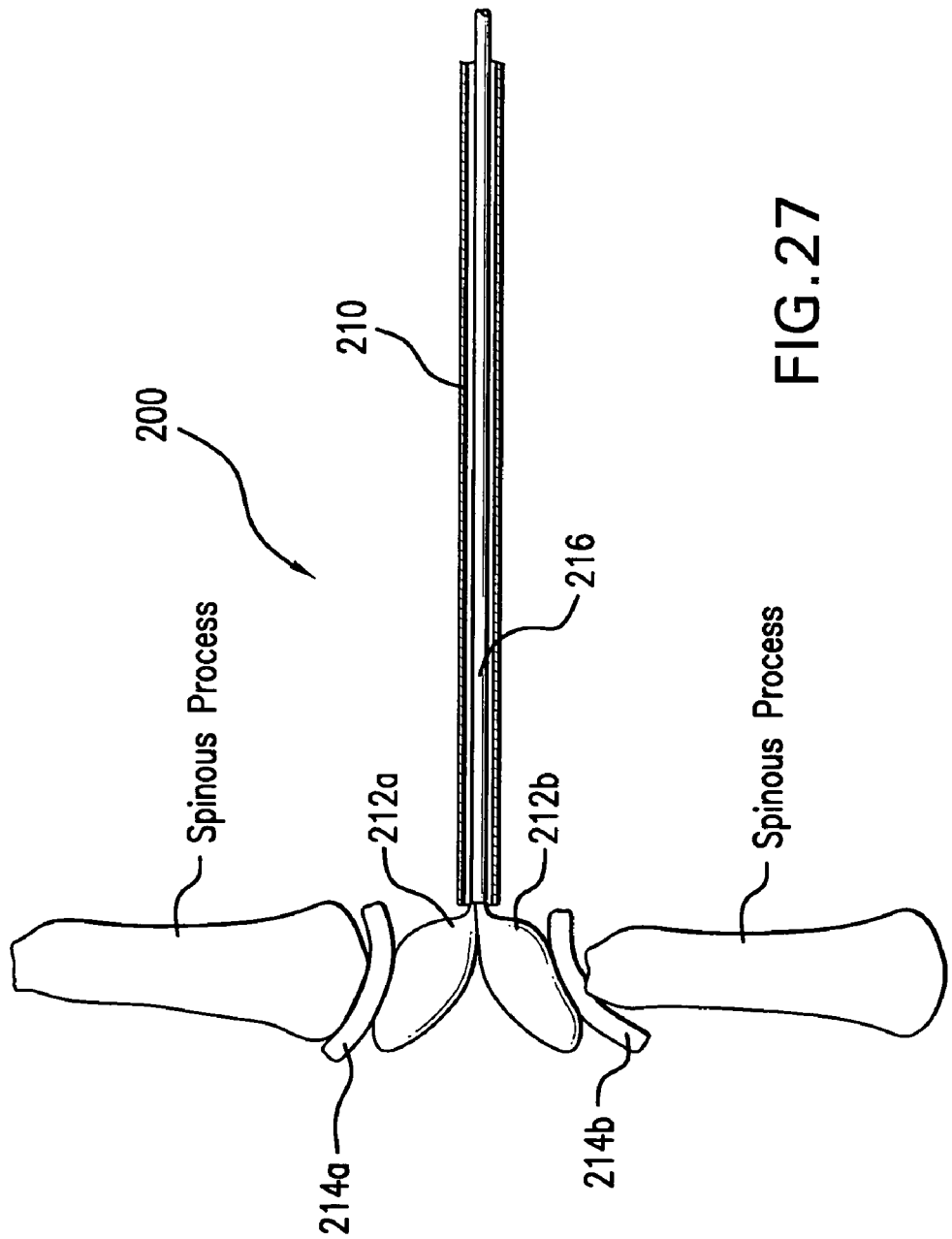
FIG. 27 is an illustration of the apparatus shown in FIG. 26 in an open or distracting position.

Referring to FIGS. 26 and 27, there is illustrated another device 200 for measuring percutaneously the optimum size of interspinous implant 10 in the closed and open positions, respectively. The measuring device 200 includes an elongated body portion 210 having a pair of jaw members 212a, 212b at the distal end thereof for positioning in the interspinous space. The jaw members 212a, 212b have respective cradles 214a, 214b adapted and configured to cup the adjacent spinous processes.

Movement of the jaw members from the closed position of FIG. 26 to the open or measuring position of FIG. 27 is controlled in a conventional manner (e.g., by oppositely angled cam slots or the like) by way of a flexible rod 216 that extends through the body portion 210, for example, similarly to plunger tube and rod as shown in FIGS. 24 and 25. Again, a measurement of the travel distance of the rod 216 within the body portion 210 may correlate to the length to which the interspinous space was distracted or even directly to the size of the appropriate implant 10. Further, a strain gauge may be used, for example by coupling the strain gauge to the plunger tube 102 or rod 216, to determine a preferable amount of force to apply.

It is also envisioned and within the scope of the subject disclosure that a temporary balloon can be inserted into the interspinous space to determine the appropriate size of implant 10 to be used. Additionally, an optimum force required for interspinous distraction could be correlated with the amount of pressure required to blow up the balloon. Thus, the size of the implant and the optimum force would be determined by how much the balloon was inflated to obtain that optimum pressure.

A Tool Kit for Percutaneous Placement the Implant

Figure 28:
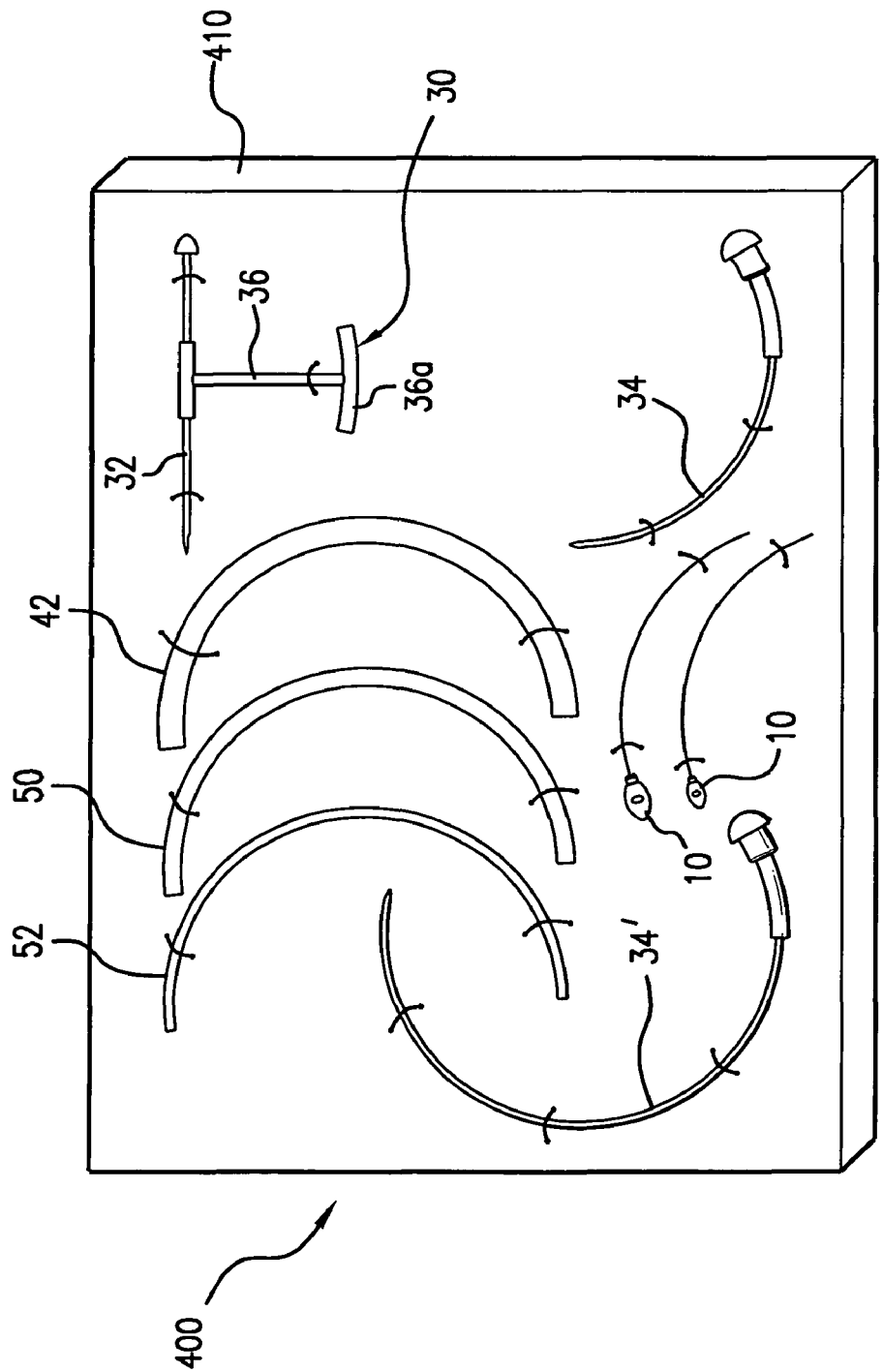
FIG. 28 is a top plan view of a tool kit for facilitating the percutaneous placement of a spinal implant.

Referring to FIG. 28, a tool kit 400 for facilitating the percutaneous implantation of the implant 10 is shown. The tool kit 400 would preferably include an enclosure 410 containing, among other things, a stylet assembly 30, which includes the elongated graduated positioning stylet 32, the curved stylet 34 and the adjustable bridging portion 36 with curved guide sleeve 36a. It is envisioned that the tool kit 400 would include either a curved stylet 34 configured for a unilateral approach to the spinous process (see FIG. 13), or a curved stylet 34' adapted and configured for a bilateral approach to the spinous process (see FIG. 18), or it could include both types of curved stylets.

The tool kit 400 may also include one or more implants 10 of varying sizes. In addition, the tool kit 400 preferably includes a set of tubular dilators (e.g., dilators 42, 50, 52) of varying diameter that correspond to the varying implants 10. The dilators may have two different lengths depending upon whether the dilators 42, 50, 52 are used in a bilateral approach procedure or a unilateral approach procedure. It is envisioned that the tubular dilators 42, 50, 52 could range from about 8 mm or less up to about 14 mm or greater. The dilators, curved stylet, and the placement tools would also have different radii of curvature to accommodate the body shape of different patients. Of course, the implants could be packaged separately for use with an insertion kit sized by the radius of curvature of the dilators, curved stylet, and the placement tools.

While the apparatus and methods of subject invention have been shown and described with reference to preferred embodiments, those skilled in the art will readily appreciate that changes and/or modifications may be made thereto without departing from the spirit and cope of the subject invention.

What is claimed is:

1. An interspinous implant for placement between spinous processes of symptomatic disc levels comprising:
   a) a shell having opposed upper and lower shell portions defining an interior cavity having four interior guide tracks that terminate in openings formed in the shell, wherein a pawl is located adjacent to each opening in the shell;
   b) four deployable ratcheting locking wings slidably coupled in a respective interior guide tracks and adapted for movement between:
      i) a stowed position in which the locking wings are disposed within the interior cavity of the shell; and
      ii) a deployed position in which the locking wings extend outward from the interior cavity of the shell through the openings formed therein, and wherein each locking wing has a set of ratchet teeth for engaging the pawl adjacent the opening through which it extends;
   c) a pair of coaxial locking wheels rotatably mounted in the shell to selectively exert a force against each locking wing to move the locking wings from the stowed position to the deployed position; and
   d) deployment cable coupled to the wheels to actuate rotation of the wheels.

2. An interspinous implant as recited in claim 1, wherein the shell is formed from a biocompatible polymeric material having a modulus of elasticity that is substantial similar to that of bone and the locking wings are formed from a lightweight, high-strength biocompatible material.

3. An interspinous implant as recited in claim 1, wherein the shell has a generally frusto-conical shape with opposing depressions.

4. An interspinous implant as recited in claim 1, wherein the lower shell portion includes a guide for accommodating a stylet during a percutaneous placement procedure.

5. An interspinous implant as recited in claim 1, wherein the deployment cable attaches to a key-shaped opening formed in the locking wheels.

6. An interspinous implant as recited in claim 1, wherein first and second wings of the four wings are located on first parallel, spaced apart geometric planes that extend on a first side of a centerline of the shell; and
   third and fourth wings of the four wings are located on second parallel, spaced apart geometric planes that extend on a second side of the centerline of the shell.

7. An interspinous implant as recited in claim 1, further comprising:
   a placement tool including:
   a) an elongated tubular stem that forms a central lumen for accommodating the deployment cable; and
   b) a coupling sleeve on a straightened distal portion of the stem for selectively engaging the shell.

8. An interspinous implant as recited in claim 7, wherein the elongated tubular stem having is curved and the coupling sleeve forms a cutting surface to sever the deployment cable.

9. An interspinous implant as recited in claim 1, further comprising:
   a mechanism for placing the interspinous implant including:
   a) a first tube having a tapered distal end with radially inwardly extending flexible prongs for engaging the shell; and
   b) second tube for insertion into the first tube to deflect the flexible prongs and, in turn, release the shell therefrom after deployment of the interspinous implant.

10. An interspinous implant as recited in claim 1, further comprising a stylet assembly for percutaneous insertion of the interspinous implant.

11. An interspinous implant as recited in claim 10, wherein the stylet assembly comprises:
   a) an elongated graduated positioning stylet for setting a position of the stylet assembly over a central axis of a spine;
   b) a curved stylet for gaining lateral access to an interspinous space; and
   c) an adjustable guide bridge having a central portion extending between the positioning stylet and the curved stylet for guiding the positioning stylet, the bridge also having a curved guide sleeve for guiding the curved stylet.

* * * * *

UNITED STATES PATENT AND TRADEMARK OFFICE
CERTIFICATE OF CORRECTION

| | | |
|---|---|---|
| PATENT NO. | : 8,075,593 B2 | Page 1 of 1 |
| APPLICATION NO. | : 12/011905 | |
| DATED | : December 13, 2011 | |
| INVENTOR(S) | : Harold Hess | |

It is certified that error appears in the above-identified patent and that said Letters Patent is hereby corrected as shown below:

Claim 1, col. 15, line 48, delete "in a respective" and replace with "in respective".

Claim 1, col. 16, line 1, delete "d) deployment" and replace with "d) a deployment".

Claim 2, col. 16, line 5, rewrite "substantial similar" to read as "substantially similar".

Claim 9, col. 16, line 41, delete "b) second" and replace with "b) a second".

Signed and Sealed this
Twenty-seventh Day of March, 2012

David J. Kappos
*Director of the United States Patent and Trademark Office*